(12) United States Patent  
Udrea et al.

(10) Patent No.: US 12,007,262 B2  
(45) Date of Patent: Jun. 11, 2024

(54) THERMAL FLUID SENSOR

(71) Applicant: Flusso Limited, Cambridgeshire (GB)

(72) Inventors: Florin Udrea, Cambridgeshire (GB); Syed Zeeshan Ali, Cambridgeshire (GB)

(73) Assignee: Flusso Limited, Cambridgeshire (GB)

( * ) Notice: Subject to any disclaimer, the term of this patent is extended or adjusted under 35 U.S.C. 154(b) by 402 days.

(21) Appl. No.: 17/354,692

(22) Filed: Jun. 22, 2021

(65) Prior Publication Data

US 2022/0120702 A1 Apr. 21, 2022

Related U.S. Application Data

(63) Continuation-in-part of application No. PCT/EP2020/079575, filed on Oct. 21, 2020.

(51) Int. Cl.
*G01N 25/18* (2006.01)
*G01F 1/688* (2006.01)
(Continued)

(52) U.S. Cl.
CPC .............. *G01F 1/6888* (2013.01); *G01F 1/69* (2013.01); *G01F 1/7084* (2013.01); *G01N 25/18* (2013.01);
(Continued)

(58) Field of Classification Search
CPC ........ G01F 1/6888; G01F 1/69; G01F 1/7084; G01F 1/698; G01F 15/022; G01F 1/6845;
(Continued)

(56) References Cited

U.S. PATENT DOCUMENTS 3,992,940 A 11/1976 Platzer, Jr.
4,944,035 A 7/1990 Aagard
(Continued)

FOREIGN PATENT DOCUMENTS

DE 19919398 A1 5/2000
EP 2157411 A1 2/2010
(Continued)

OTHER PUBLICATIONS

U.S. Appl. No. 16/658,711, Non-Final Office Action mailed on Nov. 5, 2020, 11 pages.
(Continued)

*Primary Examiner* — Freddie Kirkland, III
(74) *Attorney, Agent, or Firm* — FisherBroyles, LLP

(57) ABSTRACT

A fluid sensor for sensing a concentration or composition of a fluid, the sensor comprising: a semiconductor substrate comprising a first etched portion; a dielectric region located on the semiconductor substrate, wherein the dielectric region comprises a first dielectric membrane located over the first etched portion of the semiconductor substrate; a first heating element located within the first dielectric membrane; and a second heating element; wherein the first heating element is arranged to thermally shield the second heating element from ambient temperature changes; wherein the first heating element or the second heating element is configured to operate as a temperature sensing element; wherein the first heating element is configured to operate in a constant temperature or constant resistance mode; wherein the second heating element is configured to operate in a constant current or constant voltage mode or constant power mode; and wherein the sensor is configured to determine a thermal conductivity of the fluid using the temperature sensing element to determine said concentration or composition of the fluid.

30 Claims, 11 Drawing Sheets

(51) Int. Cl.
| | |
|---|---|
| *G01F 1/69* | (2006.01) |
| *G01F 1/7084* | (2022.01) |
| *G01N 27/04* | (2006.01) |
| *G01N 27/14* | (2006.01) |
| *G01N 27/18* | (2006.01) |
| *G01N 33/00* | (2006.01) |
| *G01F 1/698* | (2006.01) |
| *G01F 15/02* | (2006.01) |

(52) U.S. Cl.
CPC .............. *G01N 27/04* (2013.01); *G01N 27/14* (2013.01); *G01N 27/18* (2013.01); *G01N 33/0027* (2013.01); *G01F 1/698* (2013.01); *G01F 15/022* (2013.01)

(58) Field of Classification Search
CPC ........ G01N 25/18; G01N 27/04; G01N 27/14; G01N 27/18; G01N 33/0027
See application file for complete search history.

(56) References Cited

U.S. PATENT DOCUMENTS

| | | | |
|---|---|---|---|
| 5,321,983 A | 6/1994 | Nagata | |
| 5,804,720 A | 9/1998 | Morimasa | |
| 6,019,505 A | 2/2000 | Bonne | |
| 6,046,398 A | 4/2000 | Foote | |
| 6,375,279 B1 | 4/2002 | Cassidy | |
| 6,460,411 B1 | 10/2002 | Kersjes | |
| 8,667,839 B2 | 3/2014 | Kimura | |
| 8,689,608 B2 | 4/2014 | Nakano | |
| 10,288,575 B2* | 5/2019 | Ali | G01N 21/0332 |
| 10,345,130 B2* | 7/2019 | Bentley | G01F 1/6888 |
| 10,408,802 B2 | 9/2019 | Kumar | |
| 10,480,974 B2* | 11/2019 | Huang | G01F 7/00 |
| 10,488,358 B2* | 11/2019 | Udrea | G01K 7/16 |
| 10,598,621 B2 | 3/2020 | Liu | |
| 10,712,300 B2* | 7/2020 | Nakano | G01N 25/18 |
| 11,035,709 B2* | 6/2021 | De Luca | G01F 15/024 |
| 11,073,415 B2 | 7/2021 | Udrea et al. | |
| 11,639,864 B2* | 5/2023 | De Luca | G01F 1/6965 |
| | | | 73/204.25 |
| 2001/0027684 A1 | 10/2001 | Lotters et al. | |
| 2002/0100316 A1 | 8/2002 | James | |
| 2003/0041664 A1 | 3/2003 | Ariyoshi | |
| 2005/0028580 A1 | 2/2005 | Bauer et al. | |
| 2007/0011867 A1 | 1/2007 | Yao | |
| 2007/0017285 A1 | 1/2007 | Wang | |
| 2007/0113644 A1 | 5/2007 | Manaka | |
| 2007/0204688 A1 | 9/2007 | Dmytriw | |
| 2009/0016403 A1 | 1/2009 | Chen | |
| 2009/0158859 A1 | 6/2009 | Huang | |
| 2009/0164163 A1 | 6/2009 | Wang | |
| 2010/0078753 A1 | 4/2010 | Mehregany | |
| 2010/0175468 A1 | 7/2010 | Anzai | |
| 2011/0030468 A1 | 2/2011 | Chen | |
| 2011/0154885 A1 | 6/2011 | Nakano et al. | |
| 2011/0211613 A1 | 9/2011 | Hermann | |
| 2012/0216629 A1 | 8/2012 | Huang | |
| 2014/0190251 A1 | 7/2014 | Huang et al. | |
| 2014/0190252 A1 | 7/2014 | Huang et al. | |
| 2016/0025660 A1 | 1/2016 | Hepp | |
| 2016/0195419 A1 | 7/2016 | Hepp | |
| 2016/0216144 A1 | 7/2016 | Figi et al. | |
| 2018/0143051 A1 | 5/2018 | Bentley et al. | |
| 2018/0306621 A1 | 10/2018 | Hornung | |
| 2019/0030909 A1 | 1/2019 | Sato | |
| 2019/0031906 A1 | 1/2019 | Kim | |
| 2019/0301906 A1 | 10/2019 | Udrea et al. | |
| 2019/0301909 A1 | 10/2019 | Nakano et al. | |
| 2020/0080951 A1 | 3/2020 | Nakano et al. | |
| 2021/0116281 A1 | 4/2021 | Udrea et al. | |
| 2022/0120701 A1* | 4/2022 | Udrea | G01F 1/69 |
| 2022/0333966 A1* | 10/2022 | Udrea | G01N 33/0027 |

FOREIGN PATENT DOCUMENTS

| | | |
|---|---|---|
| EP | 3367087 A2 | 8/2018 |
| EP | 3392621 A1 | 10/2018 |
| GB | 2558896 A | 7/2018 |
| WO | 1998036247 A1 | 8/1998 |
| WO | 2014102086 A1 | 7/2014 |
| WO | 2021078776 A1 | 4/2021 |

OTHER PUBLICATIONS

U.S. Appl. No. 16/658,711, Notice of Allowance mailed on Mar. 24, 2021, 13 pages.
Huijsing et al., Monolithic Integrated Direction-Sensitive Flow Sensor, Institute of Electrical and Electronics Engineers Transactions on Electron Devices, vol. 29, No. 1, Jan. 1982, pp. 133-136.
Kersjes et al., An Integrated Sensor for Invasive Blood-Velocity Measurement, Sensors and Actuators A: Physical, vols. 37-38, Jun.-Aug. 1993, pp. 674-678.
Kuklinski et al., Integrated-Circuit Bipolar Transistor Array for Fluid-Velocity Measurements, Medical & Biological Engineering & Computing, vol. 19, No. 5, Sep. 1981, pp. 662-664.
Kuo et al., Micromachined Thermal Flow Sensors—A Review, Micromachines, vol. 3, No. 3, Jul. 23, 2012, pp. 550-573.
Lofdahl et al., A Sensor Based on Silicon Technology for Turbulence Measurements, Journal of Physics E: Scientific Instruments, Jun. 1989, pp. 391-393.
Moser et al., Silicon Gas Flow Sensors Using Industrial CMOS and Bipolar IC Technology, Sensors and Actuators A: Physical, vol. 27, 1991, pp. 577-581.
Nguyen, Micromachined Flow Sensors—A Review, Flow Measurement and Instrumentation, vol. 8, No. 1, Mar. 1997, pp. 7-16.
International Application No. PCT/EP2020/079575, International Preliminary Report on Patentability mailed on May 5, 2022, 8 pages.
International Application No. PCT/EP2020/079575, International Search Report and Written Opinion mailed on Jan. 22, 2021, 10 pages.
Qin-Yi et al., A Novel CMOS Flow Sensor with Constant Chip Temperature (CCT) Operation, Sensors and Actuators, vol. 12, No. 1, Jul. 1987, pp. 9-21.
Sabate et al., Multi-Range Silicon Micromachined Flow Sensor, Sensors and Actuators A: Physical, vol. 110, No. 1-3, Feb. 1, 2004, pp. 282-288.
Van Der Wiel et al., A Liquid Velocity Sensor Based on the Hot-Wire Principle, Sensors and Actuators A: Physical, vol. 37-38, Jun.-Aug. 1993, pp. 693-697.
Van Oudheusden et al., Integrated Flow Friction Sensor, Sensors and Actuators, vol. 15, No. 2, Oct. 1988, pp. 135-144.
Van Oudheusden, Silicon Flow Sensors, IEE Proceedings, Part D—Control Theory and Applications, vol. 135, No. 5, Sep. 1988, pp. 373-380.
Van Oudheusden, Silicon Thermal Flow Sensors, Sensors and Actuators A: Physical, vol. 30, Nos. 1-2, Jan. 1992, pp. 5-26.
Van Putten, An Integrated Silicon Double Bridge Anemometer, Sensors and Actuators, vol. 4, May 31-Jun. 3, 1983, pp. 387-396.
Van Putten et al., Integrated Silicon Anemometer, Electronics Letters, vol. 10, No. 21, Oct. 17, 1974, pp. 425-448.
Wang et al., MEMS-Based Gas Flow Sensors, Microfluidics and Nanofluidics, vol. 6, No. 3, Jan. 8, 2009, pp. 333-346.
Yoon et al., An Integrated Mass Flow Sensor with On-Chip CMOS Interface Circuitry, Institute of Electrical and Electronics Engineers Transactions on Electron Devices, vol. 39, No. 6, Jun. 1992, pp. 1376-1386.
EP20 793 693.1, "Office Action", Apr. 11, 2023, 7 pages.
G. De Graaf et al., "Surface-micromachined thermal conductivity detectors for gas sensing." 2012 IEEE International Instrumentation and Measurement Technology Conference Proceedings, pp. 1861-1864.
Mahdavifar et al. "Simulation and Fabrication of an Ultra-Low Power miniature Microbridge Thermal Conductivity Gas Sensor," 2014 Journal of the Electrochemical Society, 161 B55.

(56) References Cited

OTHER PUBLICATIONS

Kommandur et al., "A microbridge heater for low power gas sensing based on the 3-omega technique," Sensors and Actuators A 233 (2015) 231-238.
PCT/EP2022/067044, "International Search Report and Written Opinion", Jan. 4, 2023, 17 pages.
PCT/EP2022/067049, "International Search Report and Written Opinion", Dec. 29, 2022, 12 pages.

\* cited by examiner

THERMAL FLUID SENSOR

TECHNICAL FIELD

The present disclosure relates to a micro-machined sensor, particularly but not exclusively, the disclosure relates to a fluid sensor for sensing concentration of a fluid or concentration of components of a fluid based on thermal conductivity of the fluid.

BACKGROUND

There is an increasing demand for gas sensors to monitor pollutants in our environment. Gas sensors can be based on many different principles and technologies. One such principle is using thermal conductivity to determine the composition of gases.

For example, in G. De Graaf and R. F. Wolffenbuttel, "Surface-micromachined thermal conductivity detectors for gas sensing." 2012 IEEE International Instrumentation and Measurement Technology Conference Proceedings, pp. 1861-1864, a thermal conductivity gas sensor based on silicon technology is described.

Mandavifar et.al. in "Simulation and Fabrication of an Ultra-Low Power miniature Microbridge Thermal Conductivity Gas Sensor," Journal of the Electrochemical Society, 161 B55, describe a device comprising a suspended thin polysilicon resistor that acts as a heater and a temperature sensor as part of a thermal conductivity sensor. The change in resistance of the polysilicon with temperature allows its use as a temperature sensor.

U.S. Ser. No. 10/598,621, U.S. Pat. No. 8,667,839B2, and U.S. 63/572,279B1, U.S. Pat. No. 8,689,608 and U.S. Ser. No. 10/408,802B2 describe further sensors. Kommandur et. al., "A microbridge heater for low power gas sensing based on the 3-omega technique," Sensors and Actuators A 233 (2015) 231-238, also describes a thermal conductivity sensor.

Many of these devices use a differential signal between the main sensor and the reference. However, in all cases the reference device is a heater as well and thus doubles the power consumption of the device.

Further, many of these devices require sealing of the reference with a particular gas to use as a reference. This increases the complexity and cost of the packaging of the sensor. Further, once sealed, the sensor can only sense one particular gas (e.g. CO2) and is not applicable to sense multiple gases or multiple fluids.

Further, many of these devices suffer from ambient temperature, humidity and/or ambient pressure effects.

SUMMARY

Presently available sensors have, among others, the following disadvantages:
- high power dissipation, low sensitivity and slow dynamic response of the sensor;
- mechanical fragility and vibration sensitivity;
- reduced mechanical robustness of sensor supporting structures;
- complex fabrication processes;
- manufacturing processes that are not fully CMOS compatible; and
- manufacturing processes that are expensive.

The devices of the present disclosure are advantageous over the state-of-the-art devices for at least the following reasons:

- the sensor is able to determine composition of a fluid and concentration of different components within the fluid, in a zero or near zero flow environment;
- thermal isolation of any of the heated element which reduces power dissipation, increases sensitivity and provides a fast, dynamic response of the sensor;
- reduced mechanical fragility and vibration sensitivity of the membrane structure compared to a beam structure;
- a suitable dielectric material used for the dielectric membrane improves mechanical robustness of the membrane;
- a suitable dielectric material (with low thermal conductivity) used for the dielectric membrane (with low thermal mass) reduces power dissipation, increases sensitivity and provides a fast, dynamic response of the sensor;
- discontinuities within the membrane mitigate power dissipation, sensitivity and dynamic response issues; and the devices are fully CMOS (Complementary Metal Oxide Semiconductor) and/or MEMS (Micro-Electro-Mechanical Systems) compatible and therefore can be manufactured using fully CMOS and/or MEMS compatible processes.
- use of one of the heaters (the shielding heater) in a constant temperature or constant resistance mode to provide a very table reference against variations in the environment due to ambient temperature, humidity, ambient pressure changes.

The presently disclosed fluid sensor is able to measure the composition of the fluid based on the different thermal conductivity of each of the components of the fluid.

In general terms, the present disclosure is directed to a double heater arrangement where each heater is operating in a different mode. For example, one heater is operated in a constant temperature mode and used as a shielding heater while the second heater is operated in a constant current mode and used to generate the heat (as an active heater). By measuring the heat losses in the device, the concentration of a fluid or concentration of components of a fluid can be measured based on thermal conductivity of the fluid.

Aspects and preferred features are set out in the accompanying claims.

According to a first aspect of the present disclosure, there is provided a fluid sensor for sensing a concentration or composition of a fluid, the sensor comprising: a semiconductor substrate comprising a first etched portion; a dielectric region located on the semiconductor substrate, wherein the dielectric region comprises a first dielectric membrane located over the first etched portion of the semiconductor substrate; a first (shielding) heating element located within the first dielectric membrane; and a second (active) heating element; wherein the first heating element is arranged to thermally shield the second heating element from ambient temperature changes; wherein the first heating element or the second heating element is configured to operate as a temperature sensing element; wherein the first heating element is configured to operate in a constant temperature or constant resistance mode; wherein the second heating element is configured to operate in a constant current or constant voltage or constant power mode and wherein the sensor is configured to determine said concentration or composition of the fluid based on a thermal conductivity of the fluid.

In some implementations, as will be described in more detail below, the second heating element is located within the first dielectric membrane, or alternatively, the second heating element may be located within a second dielectric membrane, for example of the same or different dielectric region of the substrate.

The first heating element may be spatially separated from the second heating element, so that the there is a temperature difference between the first heating element and the second heating element.

A first temperature sensing element could be placed in the proximity, around, above or below the first heating element, so that the first heating element and the first temperature sensing element have the same (or largely the same) maintained temperature. Alternatively, the first heating element can be configured to sense itself the temperature such that it plays a dual role, as a heating element and as a temperature sensing element.

The first heating element could be a resistive element, in which case if operated as a temperature sensor it could be a resistive temperature detector (RTD).

The first heating element is operated in a constant temperature or constant resistance mode. This means that a bias is applied to it (current/voltage/power) and its temperature or resistance is monitored. The monitoring could be done through measuring its own temperature or resistance or by measuring the temperature or the resistance of the first temperature sensing element. Through a feedback control circuit, the temperature or the resistance of the first heating element or the first temperature sensing element is maintained constant, in spite of ambient parameter changes, such as ambient temperature, pressure, humidity etc, This ensures that the first temperature sensing element (or the heating element itself) could be used as a reference element.

The feedback control circuit may be integrated (placed on-chip), provided in the same package or be external.

The first heating element could be regarded and described as a shielding heating element or as a reference heating element as it protects the temperature or resistance of the first temperature sensing element or its own temperature or resistance from variances caused by ambient or environmental. The first sensing element could be described as a reference sensing element.

The temperature of the first heating element or sensing element could also be maintained constant even when the second heating element is in operation. Thus the power in the first heating element could be readjusted to maintain itself at constant temperature in spite of the extra heat produced by the second heating element.

The first heating element and the first temperature sensing element can operate at higher temperatures than the ambient temperature but it is envisaged that they operate at lower temperatures than the second heating element.

The second heating element may be considered as an active heating element. The second heating element can be biased through a constant current or constant voltage or constant power drive or a combination of those and its resistance and temperature may rise or fall as a function of the fluid thermal conductivity properties or as function of thermal conductivity properties of different components of the fluid and their respective concentrations.

According to a second aspect of this invention there is provided a fluid sensor for sensing a concentration or composition of a fluid, the sensor comprising: a semiconductor substrate comprising at least one etched portion; a dielectric region located on the semiconductor substrate, wherein the dielectric region comprises at least one dielectric membrane located over the first etched portion of the semiconductor substrate; a first heating element located within the first dielectric membrane; a second heating element; a first temperature sensing element positioned with the first heating element; a second temperature sensing element positioned with the second heating element; wherein the first heating element is arranged to thermally shield the first and second temperature sensing elements and the second heating element from ambient temperature changes; wherein the first heating element is configured to operate in a constant temperature or constant resistance mode; wherein the second heating element is configured to operate in a constant current or constant voltage or constant power mode, and wherein a separation between the second temperature sensing element and the first temperature sensing element introduces a temperature difference between the second temperature sensing element and the first temperature sensing element, such that a differential signal between the first temperature sensing element and the second temperature sensing element is indicative of the concentration or composition of the fluid based on a thermal conductivity of the fluid.

The second temperature sensing element could be placed in the proximity, around, above or below the first heating element, so that the second heating element and the first temperature sensing element have the same (or largely the same) maintained temperature. Alternatively, the second heating element can be configured to sense itself the temperature such that it plays a dual role, as a heating element and as a temperature sensing element.

The second heating element could be a resistive element, in which case if operated as a temperature sensor it could be a resistive temperature detector (RTD).

The monitoring of the temperature of the second heating element could be done through measuring its own temperature or resistance or by measuring the temperature or the resistance of the second temperature sensing element.

During operation of the second heating element, the heat generated by the second heater propagates into the dielectric membrane, above and below the dielectric membrane, and into the fluid surrounding the heating element. The amount of heat lost to the fluid surrounding the heating element will depend on the thermal conductivity of the fluid. Therefore, a temperature profile of the heating element will depend on the thermal conductivity of the fluid within the sensor. Dependent on the thermal conductivity of the fluid, the temperature or resistance of the second heating element or the second temperature sensing element will vary when compared to the temperature or resistance of the first heating element, or the temperature or resistance of the first heating element respectively.

As the temperature of the second heating element is dependent on the heat conducted through the fluid within the sensor and thus the thermal conductivity of the fluid, the differential signal set between the first elements (heating or sensing) and the second elements (heating or sensing) is also dependent on the thermal conductivity of the fluid. Different target fluids within the sensor have different thermal conductivities, and therefore the temperature of the second temperature sensing element (or the second heating element) can be used to determine the concentration or composition of the fluid within the sensor. The differential signal is indicative of a composition or concentration of the fluid.

The temperature or resistive change of the second temperature sensing element or the second heating element due to heat loss to the fluid is generally small compared to the measured ambient temperature. Therefore, by using a first heating element to shield the influence of the ambient temperature (and other ambient sources of noise) and keep constant the temperature or resistance of the first heating element, the differential signal setup between the first and the second elements is less affected (or virtually unaffected) by changes in the ambient temperature (and other ambient sources of noise). The differential signal can be read-out and/or amplified using an instrumentation bridge such as the Wheatstone bridge, or schemes based on differential/instrumentation amplifiers.

The first or the second heating element may operate simultaneously as both a heating element and a sensing element. The first or the second heating element can be considered as electrically equivalent to a resistor. The electrical conductivity of most heaters materials (Tungsten, Titanium, Platinum, Aluminium, polysilicon, monocrystalline silicon) varies with temperature. This variation is mostly linear and is characterised by the TCR (Temperature coefficient of resistance). The TCR can be positive or negative, but most metals have a positive and stable TCR, meaning that their resistance increases when the temperature is increased.

The advantage where heaters are used as sensing elements themselves is simplicity and reduced number of additional elements on the membrane. The larger the number of elements on the dielectric membrane, the higher the probability of impaired reliability or malfunction of the sensor.

The advantage where sensing elements are used as separate elements from the heaters is that the noise in the system is smaller and the read-out circuitry can be simplified and give higher accuracy.

It is also possible that the first heating element to be used as both heater and temperature sensor while the second temperature element to be separate from the first heating element, The fluid sensor may comprise a semiconductor substrate made of a semiconductor material such as silicon, silicon carbide or Gallium Nitride, and comprising an etched portion. The fluid sensor may also comprise at least one dielectric region comprising of oxides and/or nitrides such as silicon dioxide and silicon nitride, where the portion of the dielectric region adjacent to the etched portion is referred to as a dielectric membrane. The dielectric membrane may have embedded structures made of semiconductor material or metal structures.

The semiconductor substrate may be any semiconductor such as silicon, silicon on insulator (SOI), Silicon Carbide, Gallium Nitride or Diamond. In particular, the use of silicon is advantageous, as it guarantees sensor manufacturability in high volume, low cost and high reproducibility. The use of a silicon substrate could also enable on-chip circuitry for sensor performance enhancement and system integration facilitation. Such on-chip circuitry could be implemented by using analogue or digital or mixed-signal blocks placed outside the dielectric membrane.

The at least one dielectric membrane or multiple dielectric membranes may be formed by back-etching using Deep Reactive Ion Etching (DRIE) of the substrate, which results in vertical sidewalls and thus enabling a reduction in sensor size and costs. However, the back-etching can also be done by using anisotropic etching such as KOH (Potassium Hydroxide) or TMAH (TetraMethyl Ammonium Hydroxide) which results in sloping sidewalls. The dielectric layers within the membrane which could be formed by oxidation or oxide deposition could be used as an etch stop during the DRIE or wet etching processes. The membrane can also be formed by a front-side etch (using most commonly wet etch techniques) or a combination of a front-side and back-side etch to result in a suspended membrane structure, supported only by two or more beams. The membrane may be circular, rectangular, or rectangular shaped with rounded corners to reduce the stresses in the corners, but other shapes are possible as well.

Preferably, the semiconductor substrate may be silicon and the dielectric membrane may be formed mainly of oxide and nitride materials, or oxinitride (a pre-formed combination of oxide and nitride) and where the heater element may be made of a metal such as tungsten, titanium, copper, aluminium, gold, platinum or a combination of those or a semiconductor such as highly doped n type or p type silicon or polysilicon. The heating elements may have a shape of a meander, spiral or a hotwire.

The temperature sensing elements may have a shape of a meander, spiral or wire.

The sensing elements could be placed inside or surrounded by the heating elements; or could be placed above, or below the heating elements.

The dielectric region may comprise a dielectric layer or a plurality of layers including at least one dielectric layer. The dielectric region may comprise layers of more than one material, such as silicon dioxide, silicon nitride, or aluminium oxide. The heating element may be fully embedded or partially embedded within the dielectric membrane.

The membrane may also comprise one or more layers of spin on glass, and a passivation layer over the one or more dielectric layers. The employment of materials with low thermal conductivity (e.g. dielectrics) enables a significant reduction in power dissipation as well as an increase in the temperature gradients within the membrane with direct benefits in terms of sensor performance (e.g. sensitivity, frequency response, range, etc.). Temperature sensing elements or heaters made of materials such as monocrystalline or polycrystalline semiconductors or metals could be suspended or embedded in the dielectric membrane.

The dielectric membrane may also have other structures made of metal or other conductive or other materials with higher mechanical strength. These structures can be embedded within the membrane, or may be above or below the membrane, to engineer the thermo-mechanical properties (e.g. stiffness, temperature profile distribution, etc.) of the membrane and/or the fluid dynamic interaction between the fluid and the membrane. More generally, these structures can be also outside the membrane and/or bridging between inside and outside the membrane.

Generally speaking, a dielectric membrane region may be located immediately adjacent or above (or below if a flip-chip technology is used) to the etched portion of the substrate. The dielectric membrane region corresponds to the area of the dielectric region directly above or below the etched cavity portion of the substrate. Each dielectric membrane region may be over a single etched portion of the semiconductor substrate. The membrane maybe a "closed membrane", supported by the substrate along its entire perimeter, or can be a bridge type structure—supported by a number of dielectric beams.

The fluid sensor may be configured to sense or measure a fluid (this may be a gas but could also be a liquid), and the gas may be made of air and the components of interest could be any of $CO_2$, methane or hydrogen or other gases in dry air or humid air. The component of interest can be any fluid that has a different thermal conductivity than that of air.

The disclosed sensor could be applicable to a variety of gases and liquids, but we make specific reference to Carbon dioxide ($CO_2$), methane and hydrogen as these specific gases have thermal conductivity properties which are significantly different from those of air.

The sensor may be a thermal conductivity fluid sensor incorporated in a MEMS structure comprising a first heating element and second heating element and at least one sensing element (such as a temperature sensing element) that may be able to detect separately the fluid flow properties, such as velocity, volume flow rate, mass flow rate. The temperature sensing element may be able to also detect the composition the fluid based on the difference in thermal conductivity, specific heat capacity, dynamic viscosity, density (and other thermo-mechanical properties, hereafter simply referred to as thermal properties) of different components of the fluid.

There may be a circuit to measure a differential signal between the first and second resistive temperature elements and use it to determine the concentration of a fluid or particular fluid components based on different thermal conductivities.

The first temperature sensing element may be located a first distance away from the second heating element, and the second temperature sensing element may be located a second distance away from the second heating element, and wherein the first distance may be greater than the second distance.

The second heating sensing element may be located closer to the centre of the dielectric membrane and the first heating element may be located closer to the edge of the dielectric membrane. The two heating elements may be separated by a recessed structure to further isolate them thermally.

The first and the second heating elements may be located within the same dielectric membrane and the first heating element may surround the second heating element The first temperature sensing element and the second temperature sensing element may be located on or within the same dielectric membrane. A recessed region may preferably be located between the first temperature sensing element and the second temperature sensing element.

The first temperature sensing element and the first heating element may be located on the same dielectric membrane, and wherein the second temperature sensing element and the second heating element may be located on the same further dielectric membrane, different from the first dielectric membrane. The at least two membranes may have similar shapes and sizes.

The maintained temperature of the first temperature sensing element may be largely the same as the temperature of the first heating element and the maintained temperature of the second temperature sensing element may be largely the same as the temperature of the second heating element.

The first or second temperature sensing elements or the first or second heating elements may be located in a same layer (part of the same fabrication step) of the dielectric region and wherein the first or second temperature sensing element laterally surrounds the first and second heating element respectively, or wherein the first or second temperature sensing element is located below or above the first or second heating element respectively.

Any of the heating elements or the temperature sensing elements may be resistive and may be configured to operate as resistive temperature detectors.

The first temperature sensing element and the second temperature sensing elements may be placed on the same membrane or separate membranes. If separate membranes, the two membranes may be side by side and identical in shape. The first temperature sensing element and the second temperature sensing element may be placed in a similar position inside each of their respective membranes, to improve matching characteristics. Moreover, the first heating element may be placed together with first sensing element inside one membrane while the second heating element may be placed together with second sensing element inside a different, similar membrane. The membranes and their respective heating/sensing elements placed on the same chip may look identical and may be symmetrical to an axis on the chip. The difference is that the first heating element may be operated in a constant temperature or constant resistance mode while the second heating element may be operated in a constant voltage, constant current or constant power mode.

Alternatively each of the two membranes, mentioned above could contain two shielding heating elements (termed as first heating elements), while only one membrane may contain an active (second) heating element. In this case there are three heating elements, two (active and shield) placed on a membrane and one (shield) placed on a separate membrane. The two shielding heating elements (first heating elements) can be independent, operating at similar or different constant temperatures (or constant resistance) or could be dependent and connected in an electrical scheme or combination, such as in series or parallel and driven together by the same temperature control circuit. Both shielding heating elements are operated in a constant temperature or constant resistance mode while the second heating element may be operated in a constant voltage, constant current or constant power mode.

The second temperature sensing element may be located closer to the second heating element than the first temperature sensing element. The first temperature sensing element may be located closer to the first heating element than the second temperature sensing element. Preferably, the second temperature sensing may be located such that the second temperature sensing element has the same temperature as the second heating element during operation of the sensor. Preferably, the first temperature sensing may be located such that the first temperature sensing element has the same temperature as the first heating element during operation of the sensor.

The differential signal may be measured as a temperature difference, voltage difference, current difference, power difference, or resistor difference.

The difference in the resistance of, current through, or voltage across the two temperature sensing elements can be measured and this gives an indication of the composition of the fluid and the concentration of its one or more components. If the composition of the fluid (or concentration of a component of the fluid) around the sensor changes, its thermal conductivity also changes and this will change the thermal losses and the temperature of the second heater—in turn changing the resistance of the second resistive temperature detector, without changing (or changing insignificantly) the resistance of the first temperature resistive temperature detector, as the first heating element driven in constant resistance/temperature will shield it from any environment or ambient changes. A change in resistance could be measured directly, or could be measured as a voltage change, current change or power change.

Thus the difference in resistances (or voltages or currents) between the first and second temperature sensing elements allows measurement of the thermal conductivity of the surrounding fluid, and hence the composition of the surrounding fluid.

The first temperature sensing element and the second temperature sensing element may be both located on or within the first dielectric membrane, and the fluid sensor may comprise at least one recessed region within the first dielectric membrane configured to thermally isolate the heating element and the second temperature sensing element from the first temperature sensing element.

The second temperature sensing element may be located in a same layer of the dielectric region as the second heating element and the second temperature sensing element may laterally surround the second heating element or the second heating element may laterally the second temperature sensing element.

The first temperature sensing element may be located in a same layer of the dielectric region as the first heating element and the first temperature sensing element may laterally surround the first heating element or the first heating element may laterally the first temperature sensing element.

Alternatively, the first or second temperature sensing element may be located below or above the first or second heating element respectively.

Having the temperature sensing elements in a same layer or below or above the heating elements has the advantage that the temperature of the temperature sensing element is substantially the same of that of the corresponding heating element. This may improve the sensitivity of the sensor.

The temperature sensor element can be either laterally spaced but close to its corresponding heating element, and can be made of the same material layer as the corresponding heating element. Alternatively, the temperature sensing element may be made of a different material layer than the corresponding heating element and can be vertically spaced from the heating element, either above or below An advantage of both these configurations is that the temperature sensing element are envisaged to have substantially the same temperature as that of the heating element during operation.

The two temperature sensing elements can be identical in size, shape and resistance. Alternatively, the first temperature sensing element may be configured to have a higher resistance at room temperature than a resistance of the second temperature sensing element at room temperature, and the first temperature sensing element and the second temperature sensing element may be configured to have substantially the same resistance in operation without a fluid present or a fluid used for calibration/reference purpose.

Each of the two heating elements can have adjacent (above, below, around or in proximity) two temperature sensing elements. Thus the first heating element can be adjacent to two distinctive temperature sensing elements (termed as the first temperature sensing elements) operating at similar temperatures as the first heating element while the second heating element can be adjacent to two temperature sensing elements (termed as the second temperature sensing elements). Having two temperature sensing elements next to each heating element allows their use in a half-bridge circuitry instead of a quarter bridge circuit, thus doubling the sensitivity.

Alternatively, the first heating element may have adjacent (above, below, around or in proximity) two temperature sensing elements (of the first kind), while the second heating element may have only a single adjacent second temperature sensing element. Such a design allows a differential measurement to be made between either first temperature sensing element and the second temperature sensing element. This allows running the second heating element at two different bias levels (constant current, voltage or power) corresponding to two different temperatures. Switching between temperatures on the second heating element can improve the selectivity of the sensor. In this example, there are two temperature sensing elements next to the first heating element. However there can be more than two temperature sensing elements (of the first kind) as at this would allow simpler read-out when employing different biases of the second temperature seining element as to operate at different temperature levels Alternatively, the second heating element may have adjacent (above, below, around or in proximity) two temperature sensing elements (of the second kind), while the first heating element may have only a single adjacent second temperature sensing element. Such a design allows a differential measurement to be made between the first temperature sensing element and either of the second temperature sensing element. This allows running the second heating element at two different bias levels (constant current, voltage or power) corresponding to two different temperatures. Switching between temperatures on the second heating element can improve the selectivity of the sensor. In this example, there are two temperature sensing elements next to the second heating element. However there can be more than two temperature sensing elements (of the first kind) as at this would allow simpler read-out when employing different biases of the second temperature seining element as to operate at different temperature levels The first or the second heating element may be a resistive heating element. At least one of the first temperature sensing element and the second temperature sensing may be resistive temperature sensing elements, also known as resistive temperature detectors (RTDs).

The resistive temperature detector elements may comprise metal (Tungsten, Al, Copper, Platinum, Gold, Titanium) or semiconductor material (Silicon, Polysilicon, Silicon Carbide, Gallium Nitride, Aluminium Gallium Nitride, or Gallium Arsenide or a two dimensional electron gas)

Firstly, for increased sensitivity and stability, such resistive temperature detectors may have a high, reproducible and stable TCR (Temperature Coefficient of Resistance). Secondly, it is preferable that such resistive temperature detectors are linear in temperature (i.e. their resistance varies linearly with the temperature).

The sensing elements may be temperature sensitive and may be any of resistive temperature detectors, diodes, transistors or thermopiles, or an array in series or parallel or a combination of those.

Such sensors can be implemented in bulk CMOS, SOI (Silicon on Insulator) CMOS technology. SOI membranes can be made by using the buried oxide as an etch stop. SOI diodes, transistors and thermopiles can be made by using the thin silicon layer above the buried oxide which can be doped n or p-type.

One type of sensing element may be used or a combination of different types of sensing elements may be used.

A thermopile comprises one or more thermocouples connected in series. Each thermocouple may comprise two dissimilar materials which form a junction at a first region of the membrane, while the other ends of the materials form a junction at a second region of the membrane or in the heat sink region (substrate outside the membrane area), where they are connected electrically to the adjacent thermocouple or to pads for external readout. The thermocouple materials may comprise a metal such as aluminium, tungsten, titanium or combination of those or any other metal available in the process. Alternatively, the thermocouple materials may comprise thermocouples based on n-type and p-type silicon or polysilicon or combinations of metals and semiconductors. The position of each junction of a thermocouple and the number and the shape of the thermocouples may be any required to adequately map the temperature profile distribution over the membrane to achieve a specific performance.

The sensitivity and selectivity to the flow composition may be enhanced by using extra sensing elements, symmetrical or asymmetrical recessed regions.

There may be control circuitry that measures the differential signal between the first and second temperature sensor elements and uses it to determine the concentration of a fluid or particular fluid components based on different thermal conductivities.

A control and measurement unit/circuitry that drives the heater in constant current, constant voltage or constant power mode may be provided. The driving could be preferably in pulse mode, but continuous mode or AC mode are also possible.

The circuitry may be located on a same chip as the fluid sensor. Analogue/digital circuitry may be integrated on-chip. Circuitry may comprise IPTAT, VPTAT, amplifiers, analogue to digital converters, memories, RF communication circuits, timing blocks, filters or any other mean to drive the heating element, read out from the temperature sensing elements or electronically manipulate the sensor signals. The driving method known a 3ω may be implemented via on-chip means, or any other driving method, such as constant temperature difference and time of flight, needed to achieve specific performance (e.g. power dissipation, sensitivity, dynamic response, range, fluid property detection, etc.). In absence of on-chip circuitry, this disclosure also covers the off-chip implementation of such circuital blocks when applied to a fluid sensor. Such off-chip implementation may be done in an ASIC or by discrete components, or a mix of the two.

The circuitry may comprise one or more of:
a constant current or constant resistor drive circuit,
a constant current source,
a Wheatstone bridge,
an amplifier, an Analog to Digital convertor,
a Digital to Analog Convertor, or
a microcontroller.

Differential signals can be obtained by using a combination of current sources and differential amplifiers, bridge type circuits or other types of subtraction circuits or instrumentation amplifiers.

The first temperature sensing element and the second temperature sensing may be located on two sides of a bridge circuit (also referred to as an instrumentation bridge, and can be a Wheatstone bridge), and the sensor may be configured such that an output of the bridge circuit may be a function of the thermal conductivity of the fluid around the sensor. The output of the bridge circuit may therefore also be a function of the concentration of particular fluid components with different thermal conductivities.

The first temperature sensing element and second temperature sensing element may be placed together with other components on the sides of an instrumentation bridge, such as a Wheatstone bridge, and the differential output of the bridge could be a function of the thermal conductivity of the fluid around the sensor and the concentration of particular fluid components with different thermal conductivities. Such differential signals can be further amplified by using amplifiers, either located on the same chip, to maintain low noise, or placed within the same package, module or system.

The fluid sensor may comprise at least one recessed region within the at least one dielectric membrane. The recessed region may be located between the first temperature sensing element and the second temperature sensing element—therefore there is a greater recessed volume between the second heating element and the first temperature sensing element than between the second heating element and the second temperature sensing element, such that the recessed region introduces a temperature difference between the first temperature sensing element and the second temperature sensing element due to differences in heat conduction through the dielectric membrane.

There may be no recessed region between the heating element and their respective temperature sensing element so that the temperature element is at substantially the same temperature as the corresponding heating element during operation of the device.

There may also be recessed regions between the first sensing element and the edge of the membrane. This is to minimise the power consumption of the first heating element.

The recessed regions or discontinuities in the dielectric membrane provide an interruption (or partial interruption) in the thermal conduction path through the solid of the dielectric membrane. This in turn will mean that the heat path will occur more through the fluid above the recess (via conduction and convention) or through the cavity space formed as a result of the recess (mainly through fluid conduction). In both cases (heat above the cavity space or within the cavity space), the heat dissipation will depend on the thermal conductivity of the fluid. This increases the sensitivity of the differential signal to the thermal conductivity of the fluid.

The at least one recessed region may comprise one or more discontinuous regions where the thickness of the dielectric membrane is discontinuous or varies from an average or most common dielectric membrane thickness.

The at least one recessed region may be located between the heating element and an edge of the dielectric membrane.

An edge of the dielectric membrane may refer to a perimeter edge of the dielectric membrane, in other words, the area where the dielectric membrane meets or joins the semiconductor substrate. The area of the dielectric region above the semiconductor substrate may refer to the area of the dielectric region outside the dielectric membrane.

The recessed region may be located between the first or the second heating element and the edge of the dielectric membrane. In particular, the recessed regions maybe defined such that there is at least one recessed region between the second heating element and the first heating element and there may be at least one further recessed region between the first heating element and the edge of the membrane or alternatively they may be no recessed regions between the first heating element and the edge of the membrane.

The recessed regions may be holes (perforations) through the dielectric membrane. This would be advantageous, as the thermal conduction path through the solid of the dielectric membrane will be impeded and this will mean that the thermal conduction will occur through the holes (mainly via conduction) or above the holes (via both conduction and convection), thus facilitating the measurement of the composition of the fluid based on the different thermal conductivity of each of the components of the fluid.

There may be at least one hole through the membrane to connect the upper side of the membrane to the lower side of the membrane via the fluid to be sensed. The at least one hole also disrupts the thermal conduction path through the solid dielectric membrane, forcing more heat to dissipate via convection and conduction through the environment. The presence of the at least one hole also helps to reduce the power consumption of the device (for the same heater temperature), because of the reduction in the heat conduction losses (through the solid membrane). Furthermore, the presence of the at least one hole allows for a lower thermal mass of the membrane thus reducing the time needed for the heater to heat up and cool down.

The at least one hole or recessed region may be used to enhance the sensitivity/selectivity to any fluid or component of the fluid (e.g. air with a concentration of $CO_2$) with a thermal conductivity that is different to that of a reference fluid or another component of the fluid (e.g. air).

An arrangement and specific design of different holes and different sensing elements is provided to enhance the sensitivity to any fluid or component of the fluid (e.g. air with a concentration of $CO_2$) with a thermal conductivity that is different to that of a reference fluid or another component of the fluid (e.g. air).

The arrangement of different holes or slots (or recessed regions) may be placed symmetrically around the heating element and the second temperature sensing element.

The at least one recessed region may comprises one or more holes. The holes may refer to apertures, perforations or slots extending through an entire height or depth or thickness of the dielectric membrane. This forms a fluid flow path and provides fluid connection between area above and area below membrane.

The at least one of the one or more holes may comprise an elongate slot extending towards opposite edges of the dielectric membrane. The elongate slot may not extend completely to the edges of the dielectric membrane or completely isolate the dielectric membrane either side of the elongate slot. The elongate slot increases thermal isolation across a width of the dielectric membrane of the device. Optionally the elongate slot may be extending in a same direction as one or more heating elements and/or sensing elements. The elongate slots may be, for example, rectangular, square, or semicircle.

The one or more holes may comprise an array of perforations. The perforations may comprise individual holes significantly smaller than a width of the dielectric membrane of the device. The array of perforations may can extend substantially across a width of the device.

The at least one recessed region may comprise a partial recess within the dielectric membrane. The partial recess or trench may extend from a top surface of the dielectric membrane or may extend from a bottom surface of the dielectric membrane. The partial recess may extend partially through a height or depth or thickness of the dielectric membrane. The at least one perforation may be in the form of a trench formed from the top or the bottom surface but not penetrating the other surface.

The discontinuities may be referred to as a gap in the membrane from the top surface to the bottom surface. Though, not as effective in terms of the thermal performance, a discontinuity could also refer to a trench or partial hole created from either the top or the bottom surface (if an upside-down membrane is used) without penetrating the other surface. The advantage of such partial holes is that they could impact less the mechanical strength of the membrane and in some cases they may be easier to be manufactured. Moreover, such partial holes could be used to hermetically seal the bottom side of the membrane or allow no fluid penetration below the membrane.

The at least one recessed region may have a meander shape. In other words, the discontinuity may have a non-standard shape such as a concertina or corrugated shape formed of a series of regular sinuous curves, bends, or meanders.

The etched region of the semiconductor substrate may have sloped sidewalls. The etched region of the semiconductor substrate may not extend through the entire depth of the semiconductor substrate.

The semiconductor substrate may comprise an additional etched portion, and the dielectric layer may comprise an additional dielectric membranes located over the additional etched portions of the semiconductor substrate. The sensor may further comprise additional heating elements located within the additional dielectric membrane, and additional temperature sensing elements.

Additional first/second heating/sensing elements can play a similar role of the first/second heating/sensing elements respectively.

The additional first/second/heating/sensing elements may be connected in series respectively. Each of the first heating/sensing elements can be operated substantially at the same temperature, while each of the second heating/sensing elements can be operated substantially at the same temperature (different from the temperature of the first elements).

In this case, a differential signal between the series combination of the first sensing temperature elements and the second first sensing temperature elements is obtained and used to determine the concentration of a fluid or particular fluid components based on different thermal conductivities. This allows the sensitivity of the sensor to be increased (by scaling up with the number of membranes, heating elements, and temperature sensing element) and also lowers the minimum resolution of the concentration of a particular gas component that can be sensed based on its difference in thermal conductivity compared to the rest of the fluid.

The additional heating/sensing elements may be configured to operate at different temperatures.

Each first/second heating element in combination with a corresponding first/second temperature sensing element may operate independently and preferably at different temperatures to improve selectivity to different gases. Alternatively the second heating elements in combination with second temperature sensing elements are operated at different temperatures while the first heating elements in combination with first temperature sensing elements are operated at the same reference temperature above the ambient.

The second heating element(s) may be driven at more than one temperature, to increase the selectivity of the device. Gas thermal conductivity varies with temperature, and this variation is different dependent on the gas. In one drive mode, the second heater can be driven at a temperature where the thermal conductivity of air and carbon dioxide are identical, and then used to detect another gas (e.g. hydrogen or methane). In this scenario, there will be known unwanted response from present carbon dioxide and thus the selectivity of the device is improved. The second heater can also be run at the temperature that provides the optimum sensitivity for the gas that is being measured.

The fluid sensor may comprise an array of multiple dielectric membranes located over multiple etched portions of the semiconductor substrate, each membrane having: a first/second heating element located within the dielectric membrane; a first/second resistive temperature detector element located in the proximity of the first/second heating element respectively and within the dielectric membrane. The first heating elements can be operated in constant temperature/constant resistance mode, while the second heating elements can be operated in a constant current, constant voltage or constant power mode. A differential signal may be measured between the at least one first temperature sensing element and the at least one second temperature sensing element such that the differential signal is a function of the thermal conductivity of the fluid around the sensor and the concentration of particular fluid components with different thermal conductivities.

The array may contain one or several first resistive temperature detectors outside the dielectric membrane. These may play the role of ambient temperature sensing or may be used in bridge configurations for matched resistors.

The fluid sensor may further comprise a covering located on a surface of the sensor, where the covering may comprise a hole configured to allow fluid travel from an outer surface of the covering to a fluid channel above the dielectric membrane.

The fluid sensor may further comprise a further temperature sensing element located outside the membrane region. The further temperature sensing element may be thermally isolated from the heating element.

An additional or further temperature sensing element(s) may be placed outside the dielectric membrane as a reference ambient temperature sensing element to measure the ambient temperature or the temperature of the fluid, and the signal from the further temperature sensing element may be used for temperature compensation for a more accurate calculation of the concentration of one or more specific components of the fluid.

The reference ambient temperature sensing element (resistive temperature detector) could be used as part of a combination sensor (or a sensor fusion system) to read multiple physical properties of the environment (fluid composition and concentration of different components, fluid temperature or ambient temperature, or fluid velocity of fluid flow rate). Alternatively, a separate temperature sensor could be integrated on-chip as an extra resistive temperature detector, a diode or a transistor. An ambient temperature sensor could also be provided as part of the ASIC as a VPTAT or IPTAT sensor based on bandgap reference.

The temperature compensation can be done by using both the temperature reading from the additional ambient temperature sensing element and the differential reading between the first and second temperature sensing elements. This can be implemented by either a formula (within an algorithm) to adjust the final reading, or using a look up table and interpolation to determine the final reading.

The reference ambient temperature sensing element may be used to set the temperature of the first heating/sensing element, to optimise its power consumption. For example the ambient temperature could be specified to be between −40° C. to 70° C. The first heating element could be set to operate in constant temperature at 80° C. (higher than any possible ambient temperature) while the second heating element could be set to operate variably between 120-250° C.

Alternatively, the reference ambient temperature sensing element may first determine the actual ambient temperature and set the first temperature sensing just above the ambient (say by 20° C., to accommodate enough variations in the ambient temperature). The ambient temperature may be monitored before any cycles of measurements or at fix intervals. For example if the sensor operates at an ambient temperature close to the room temperature (25° C.) the first heating element may be set at a constant temperature of 45° C. In this way the power consumption may be optimised. The second heating element may be driven in constant current/voltage/power at an initial temperature much higher than the first heating element (for CO2 detection this could be in the range of 150-250° C.).

The fluid sensor may further comprise a pair of temperature sensing elements located on the dielectric membrane, wherein a first temperature sensing element of the pair of temperature sensing elements may be located on a first side of the second heating element and a second temperature sensing element of the pair of temperature sensing elements may be located on a second side of the second heating element.

The device is able to simultaneously sense properties of the fluid flow such as speed, mass, volume, shear stress as well as the composition of the flow (e.g., whether the fluid, in this case, the gas, has a certain $CO_2$ or hydrogen or methane percentage/ppm within air).

Therefore, the fluid sensor may comprise a first pair of sensing elements and a second pair of sensing elements, and a differential signal between the first pair of further sensing elements may be configured to measure a property of a composition of the flow (such as different components of the fluid and their concentrations based on their different thermal conductivities), and a differential signal between the second pair of sensing elements may be configured to measure a flow property (such as flow rate, flow direction, velocity or flow mass or flow volume rates).

The flow could be measured by employing the pair of temperature sensing elements displaced on either side of the heating element within the same dielectric membrane, and optionally used as a differential pair. The differential pair may be formed of one upstream sensing element and one downstream sensing element.

Holes or discontinuities (also referred to as recessed regions) may be placed so that they affect less the differential signal between the pair of temperature sensing elements that measure the properties of the flow but they affect significantly more the differential signal between the sensing elements that measure the composition of the flow.

According to a further aspect of the disclosure, there is provided a sensor assembly comprising the fluid sensor as described above and an application specific integrated circuit (ASIC) coupled to the sensor.

The control circuitry can be located on the same chip as the sensor (monolithically integrated), or can have an application specific integrated circuit (ASIC) coupled to the sensor. The ASIC can be on a separate chip, but within the same package, as a hybrid, co-packaged or using system in package (SIP) solutions. Alternatively, the ASIC could be placed outside the package, on a PCB (Printed Circuit Board) or within the same case/box.

The ASIC may be located underneath the sensor, for example using a die stack technique. Alternatively, the ASIC may be located side by side with the sensor or elsewhere. The ASIC may be connected to the sensor using wire bonding and pads, or using through-silicon-vias (TSV) extending through the semiconductor substrate. Alternatively, the sensor and the ASIC can be located on the surface of a common PCB or embedded in a PCB.

An ASIC may be provided within the same system or the same package or on-chip to provide electronic circuitry to drive, read-out signals and process signals from the sensor. The ASIC may be placed in a stack die configuration under the sensor and the sensor and ASIC are placed within a manifold or an open package, to allow contact to the fluid.

According to a further aspect of the disclosure, there is provided a sensor assembly comprising a sensor housing; and a fluid sensor as described above located within the flow sensor housing.

The fluid sensor housing may comprise an inlet and an outlet, and a fluid flow path for directing a fluid flow through the sensor. The sensor may be packaged within a packaging house or manifold with an inlet, outlet and a channel to provide more accurate measurements of the flow or the composition of the fluid.

According to the same or a further aspect of the disclosure, there is provided a sensor assembly comprising the fluid sensor as described above, wherein the fluid sensor may be packaged on a printed circuit board in a flip-chip configuration.

The device may be packaged in a metal TO type package, in a ceramic, metal or plastic SMD (surface mount device) package. The device may also be packaged directly on a PCB, or with a flip-chip method. The device may also be embedded in a substrate, such as a customised version of one of the previously mentioned package, a rigid PCB, a semi-rigid PCB, flexible PCB, or any other substrate, in order to have the device surface flush with the substrate surface. The package can also be a chip or wafer level package, formed for example by wafer-bonding.

In particular, the package maybe designed such that there is a surface very close to the membrane, for example in a flip-chip scenario, such that the surface is less than 50 um from the membrane. This increases the power loss through the fluid and improves the sensitivity of the sensor.

According to a further aspect of the disclosure, there is provided a method of measuring a concentration or composition of a fluid using a fluid sensor as described above, the method comprising: applying an electrical bias, in the form of constant current/constant voltage/constant power to the second heating element; applying an electrical bias to the first heating element with a control loop mechanism to maintain constant temperature or constant resistance and monitoring a differential signal between first and second sensing elements to determine the concentration or composition of the fluid based on thermal conductivity of the fluid.

Applying an electrical bias to the second heating element may comprise applying an electrical bias such that the differential signal between the first temperature sensing element and the second temperature sensing element may be minimised. Minimised may refer to reducing the differential signal to zero or substantially zero.

The electrical power, current, or voltage applied to the second heating element may be adjusted to bring to zero or substantially zero the differential signal between the first and second temperature detector elements (by varying the heating element power, current, or voltage could be such that the resistances of the two temperature detectors or the voltages across the temperature detectors are equal). This may be done during the calibration of the sensor or during the operation of the sensor. This could be set as calibrated point, giving a zero differential signal. Alternatively, this could be set during the operation and the heater power/current/voltage could be measured as an indication of the fluid compositions or the concentration of its components The change in the electrical power, voltage or current through the second heater may be monitored to measure one or more concentrations of specific components of the fluid based on their different thermal conductivities.

The first and second temperature sensing elements, and optionally the corresponding heating elements, may be connected to a differential amplifier or a Wheatstone bridge type circuit such that the differential signal may be used to measure one or more concentrations of specific components of the fluid based on their different thermal conductivities.

The measurement of the differential signal (for example, the differential resistance) can be performed in a number of ways. A first way is to apply a constant current to both the first and second temperature sensing elements (temperature resistive detectors) and measure the voltage difference between them using a differential amplifier. A further method is to use a Wheatstone bridge or other type of bridges. For both these methods, a calibration can be done initially to set a zero point value. This can either set a differential voltage value when the target fluid (or component of the target fluid) is not present, or modify the current to one of the resistors to ensure the differential voltage is at zero when the target fluid is not present. Alternatively, the calibration can be done initially to set a zero point value of the differential signal when the component of the fluid (e.g. $CO_2$) is known (e.g. 400 ppm of $CO_2$ in air) by using an external precision CO2 device (e.g. NDIR sensor).

The method may comprise driving the first/second heating element in pulse mode or AC mode to modulate the temperature of the heating element to vary the differential signal; and using the differential signal to selectively differentiate between different fluid components and/or determine the concentration of the different components.

The temperature of the second heating element may be modulated by varying the current, voltage or power to different levels and/or with different electrical pulses such as to vary the differential signal between the first and second resistive temperature detectors in order to selectively differentiate between different fluid components and/or to provide information regarding the concentration of such components.

The temperature of the second heater may be modulated and the voltage difference between the first and second temperature sensing elements at different temperatures may be assessed against reference values, and the difference between the two may be indicative of the flow composition.

The second heating element temperature may be modulated by applying different power levels to increase sensitivity and selectivity to different fluid components based on their thermal conductivity variation with temperature. For example, the difference between the thermal conductivities of $CO_2$ and the air is higher at room temperature than at high temperatures. The opposite is true for Methane, so the difference between the thermal conductivities of methane and the air is lower at room temperature than at high temperatures. Hydrogen has also a different variation of the thermal conductivity with temperature than that of $CO_2$ or air. By running the second heater at different temperature levels (i.e. modulating the temperature of the heater), it is entirely possible to differentiate between the contributions of different concentrations of fluid components in the fluid. In this way, for example, Hydrogen and $CO_2$ contributions can be decoupled and their concentration values can be found.

The first/second heater (also referred to as the first/second heating element) may be operated in a pulse mode (e.g. driven with a square wave, sinusoidal wave, Pulse Width Modulated wave (PWM), Pulse Density Modulation, etc.) or continuous mode. The pulse mode has, among others, the advantage of reduced power consumption, reduced electromigration for enhanced device reliability/lifetime, and improved fluid properties sensing capabilities. Pulses could be used in different polarities to further reduce the impact of electromigration on the heating element.

Different drive modes and measurement modes are possible. For example, the first/second heater can be driven using PWM, and the off time of the PWM can be used to measure heater resistance, and/or differential signal. This measurement can be done in a very short time, faster than the thermal time constant of the membrane to avoid self-heating.

Selectively differentiating between different fluid components and/or determining the concentration of the different components may comprise using a neural network.

An algorithm containing machine learning and artificial intelligence may be implemented. For example, the sensor or a fluid sensing system may further comprise a controller or a processing system comprising a neural network. The neural network may be trained using data from different known gases or mixture of gases at different temperatures. The use of a trained neural network to identify known gases or a mixture of gases can improve accuracy, sensitivity and selectivity of the fluid sensor.

The neural network may be trained to recognise the composition of a gas mixture based on the differential signal between the first and second temperature sensing elements. The neural network could be trained using supervised learning based on a set of data of sensor output values for known gas mixtures at a set of heating element temperatures. The inputs to the neural network could be the sensor output values at a predetermined set of temperatures. The neural network may be configured to process each differential signal from the first and second temperature sensing elements in order to determine the components of the gas mixture and the concentrations of each component in the gas mixture. The outputs from the neural network could be the fraction of each gas in the mixture. Synthetic training data could be generated to enhance the training by providing, for example, many more combinations of gases than would be practically realisable in a real laboratory. A support-vector machine could be trained to discriminate between different gases.

The method may comprise: applying a modulated function to the second heating element, while keeping the first heating element at constant temperature above the ambient, measuring the modulation, the time delay, or the phase shift of the differential signal between the first temperature sensing element and the second temperature sensing element; and determining a concentration or composition of the fluid using the measured modulation, time delay or phase shift.

The first/second heaters or the first/second temperature sensing elements can be biased with a transient signal (e.g. AC, square wave, pulsed, step). Using transient based signals, the thermal diffusivity can be determined using the measured values from the first and second temperature sensing elements. In this way, more information can be extracted from the environment.

In a method of transient fluid sensor drive modes, a step change in input current can be applied to the second heater and the time constant for the temperature rise in the second heater or second temperature sensing element can be measured. This time constant can give information about the thermal conductivity and diffusivity of the environment. Both can be used to identify gas concentration.

In another method of transient sensor drive modes, a sinusoidal wave can be applied to the second heater. The change in amplitude and change in phase shift can provide information on thermal conductivity and thermal diffusivity, thus providing information on the gas concentration.

Any of the temperature sensing elements may be driven in short pulses of power, voltage or current. The temperature sensing elements (resistive temperature detectors) may be driven in a pulse mode (e.g. driven with a square wave, sinusoidal wave, Pulse Width Modulated wave, Pulse Density Modulation, etc.) or continuous mode. The pulse mode has, among others, the advantage of reduced self-heating of the temperature sensing elements, which minimises the noise and increases the sensitivity or the signal to noise ratio. This is particularly important for the second sensing temperature element (which is closer to the heating element), which suffers more from the self-heating effect than the first temperature element.

Whilst several methods are described, any other method of driving the sensor that can provide information on the environment that is being measured may be used.

According to a further aspect of the present disclosure, there is provided a fluid sensing system comprising a fluid sensor as described above; and a controller configured to perform a method as described above.

The fluid sensing system may include a hardware or software interface wherein an algorithm is implemented to facilitate to selectively differentiate between different fluid components and/or to provide information regarding the concentration of such components.

A software algorithm configured to perform any of the methods as described above could be implemented to differentiate between these components and increase sensitivity related to each of the components of the fluids. The software algorithm could be implemented in a local microprocessor. Calibrated data could be stored in a memory device or integrated circuit. Alternatively, the software could be incorporated within an ASIC and driving of the sensor and processing of the signal could be done within an ASIC.

Processing of the signal could also be done remotely in a sensor hub, or on an external server accessed using the Internet (for example, the cloud).

Sampling and averaging of the data, as well as ways to remove outliers from the data could also be used as part of an algorithm and could be implemented in hardware using different electronic components such as micro-controllers, memories or could be done using an ASIC.

Readings from the sensor may be averaged in several ways, for example using a moving mean average or a moving median average. A moving mean average is useful for removing random noise from the signal. A moving median average is useful for removing outliers.

According to a further aspect of the present disclosure, there is provided a method of manufacturing a fluid sensor as described above, the method comprising: forming at least one dielectric membrane located over a first etched portion of a semiconductor substrate semiconductor substrate comprising a first etched portion; forming a first (shielding or reference) heating element located within the at least one dielectric membrane; forming a second (active) heating element located within the at least one dielectric membrane or a further dielectric membrane, forming a first temperature sensing element in the proximity of a first (shielding) heating element located within at least one dielectric membrane, forming a second temperature sensing element in the proximity of the second (active) heating element located within a first dielectric membrane or a further dielectric membrane; wherein the first heating element is operated in a constant temperature or constant resistance mode; and wherein the second heating element is operated in a constant current or constant voltage mode or constant power; and wherein the separation between the second temperature sensing element and the first temperature sensing element introduces a temperature difference between the second temperature sensing element and the first temperature sensing element, such that a differential signal between the first temperature sensing element and the second temperature sensing element is indicative of the concentration or composition of the fluid based on a thermal conductivity of the fluid.

BRIEF DESCRIPTION OF THE FIGURES

Some embodiments of the disclosure will now be described by way of example only and with reference to the accompanying drawings, in which.

DETAILED DESCRIPTION OF THE PREFERRED EMBODIMENTS

Some examples of the disclosed device are given in the accompanying figures.

Figure 1:
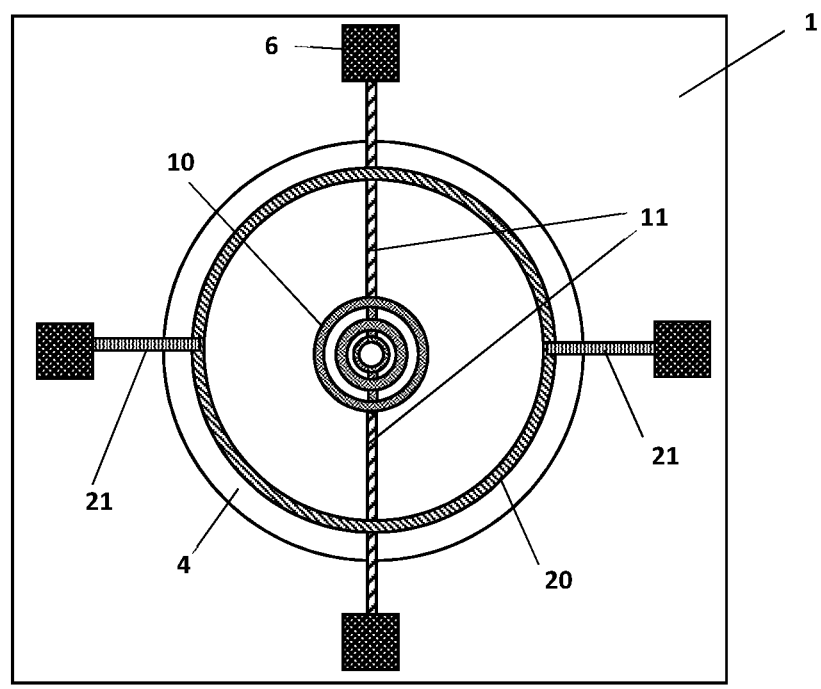
FIG. 1 shows the top view of a thermal conductivity fluid sensor with first and second circular heating elements on a circular membrane, where the heating elements also act as temperature sensing elements.

FIG. 1 shows a top view of a thermal conductivity fluid sensor. The sensor chip 1 comprises a circular dielectric membrane 4. There is a first resistive heating element 20, in a ring shape connected to bond pads 6 by tracks 21. There is also a second resistive heating element 10 connected to bond pads 6 by means of tracks 11. The second heating element is in the centre of the membrane while the first heating element is closer to the edge of the membrane (near the periphery of the membrane). The two heating elements also act as temperature sensing elements. During operation there may be provided circuitry to heat the first temperature sensing element to a temperature above ambient in a constant temperature mode or constant resistance mode. The second temperature sensing element (which is in this configuration the same as the second heating element) may be configured to operate in constant current/voltage/power mode, with the current/voltage/power chosen such that it is at a target temperature higher than the temperature of the first heating element.

In such a configuration, the temperature of the second heating element 10 stays constant with changes in ambient temperature. This is because the first heating element 20 stays at a constant temperature and the power consumption requirement of the second heating element 10 then becomes dependent on the temperature of the first heating element rather than the ambient temperature. In this way, the effect of ambient temperature can be cancelled out during the sensor measurement (or largely minimised). In other words, the first heating element 10 acts as a shield against variations in ambient temperature and providing a useful reference in the read-out circuit.

However if there is a change in the composition of the fluid surrounding the sensor, then the thermal conductivity of the fluid will change, causing a change in the power consumption required by the second heating element, 10. Since the second heating element 10 is operated in constant current/voltage/power mode, the temperature of the second heating element will change, and this change in temperature can be used to determine the composition of the fluid present. For example, carbon dioxide has a lower thermal conductivity than air. If the surrounding fluid is air, and the concentration of carbon dioxide increases, then the power required by the second heating element will decrease, and/or its temperature will rise.

The temperature can be measured by measuring the change in the resistance of the second heating element. A Wheatstone bridge can be used to measure the differential change in resistance of the second heating element as compared to the resistance of the first heating element. The resistance of the first heating element will stay constant as it is operated in a constant temperature mode so the temperature of the first heating element does not change, and hence the resistance does not change.

Since the heating element and temperature elements are the same, the circuitry needs to be carefully configured to allow the elements to do both. In one circuit configuration, the temperature measurement circuitry also provides the heating power required by the heating element. In another configuration, electronic switches (for example comprising transistors) are used to switch the elements between driving circuitry and temperature/resistance measurement circuitry. Thus, the heating elements would be operated as a heater normally would be, but when the measurement needs to be made, it is switched for short time to the measurement circuitry. The measurement time is envisaged to be shorter than the thermal time constant of the membrane to avoid the measurement affecting the temperature.

Figure 2:
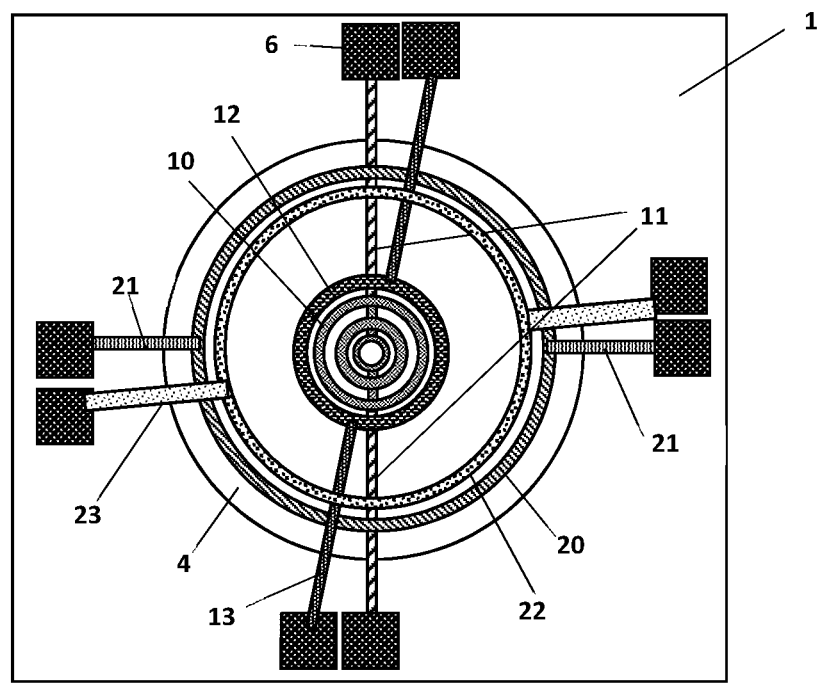
FIG. 2 shows the top view of a thermal conductivity fluid sensor with first and second circular heating elements on a circular membrane, and also separate temperature sensing elements.

FIG. 2 shows the top view of a thermal conductivity fluid sensor comprising temperature sensing elements separate from the heating elements. There is a first temperature sensing element 22 next to the first heating element 20, and a second temperature sensing element 12 next to the second heating element 10. Tracks 23 connect the first temperature sensing element 22 to bond pads 6, while tracks 13 connect second temperature sensing element 12 to other bond pads 6. Having the heating and temperature sensing elements makes the circuitry easier as no switching is required. In addition, the noise created by the heater could be minimised.

In FIGS. 1 & 2, the first and second heating elements, and the first and second temperature sensing elements appear to be on different material layers due to position of tracks and interconnects. However, it is envisaged that they may all be within the same material layers.

Figure 3:
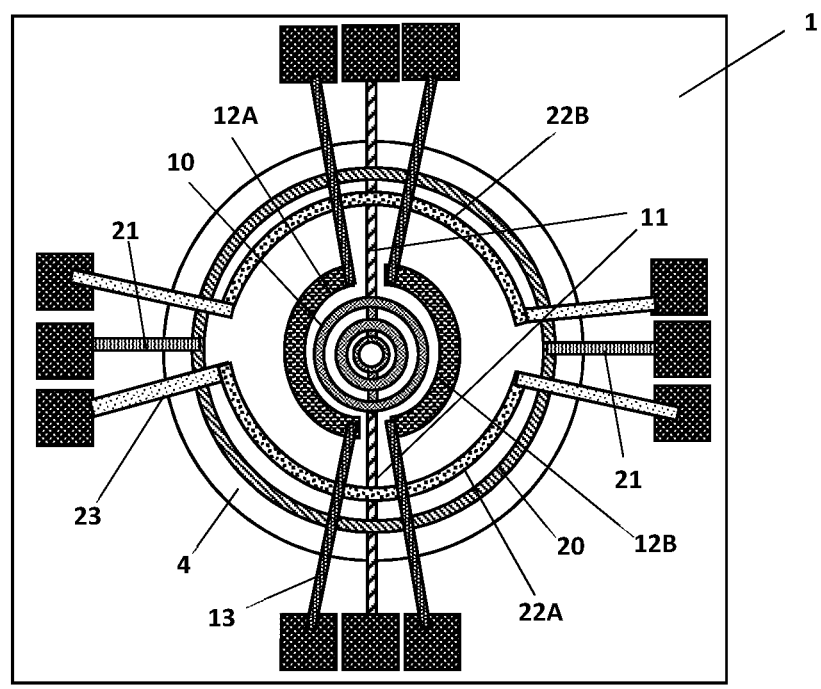
FIG. 3 shows the top view of a thermal conductivity fluid sensor with two temperature sensing elements next to each of the first and second heating elements.

FIG. 3 shows the top view of a thermal conductivity fluid sensor where there are two temperature sensing elements next to each heating element. The first heating element 20 has temperature sensing elements 22A and 22B next to it, while the second heating element 10 has temperature sensing elements 12A and 12B next to it. Sensing element 22A has similar resistance to 22B, while sensing element 12A has similar resistance to 12B. Having two temperature sensing elements next to each heating element allows their use in a half-bridge circuitry instead of a quarter bridge circuit, thus doubling the sensitivity.

Figure 4:
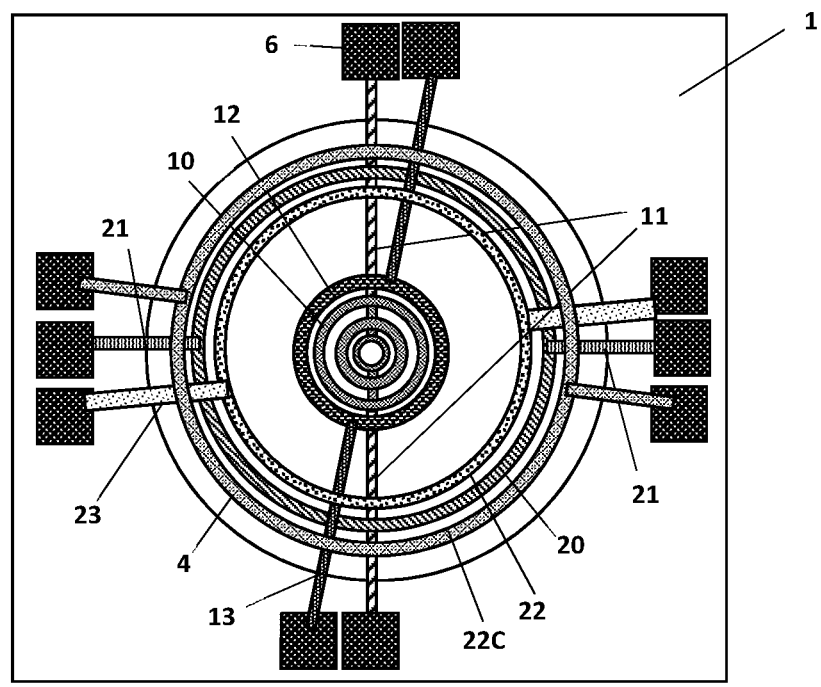
FIG. 4 shows the top view of a thermal conductivity fluid sensor with two temperature sensing elements next to the first heating element and one temperature sensing element next to the second heating element.

FIG. 4 shows the top view of a thermal conductivity fluid sensor where there is one temperature sensing element 12 next to the second heating element 10, but two dissimilar resistive temperature sensing elements 22, 22C next to the first heating element 20. Such a configuration allows a differential measurement to be made between either temperature sensing element 12 and 22, or between 12 and 22C. This allows the running of the second heating element at two different bias levels (constant current, voltage or power) corresponding to two different temperatures. Switching between temperatures on the second heating element can improve the selectivity of the sensor. Because the resistive temperature sensing elements 22 and 22C are next to the first heating element 20 which is operated in constant temperature mode, their temperature, and hence resistance will always stay constant. However the resistance of temperature sensing element 12 will change with changes in temperature of the second heating element (at the two different biases resulting in two different temperatures—temperature T1 and temperature T2). The resistive temperature element are designed such that elements 12 and 22 have the same resistance when the second heating element is at temperature T1, while the elements 12 and 22C have the same resistance when the second heating element is at temperature T2. So when the second heating element is at temperature T1, a differential measurement can be made between elements 12 and 22, and when it is at temperature T2 a differential measurement can be made between elements 12 and 22C. For the differential measurements, it is envisaged that resistances of the two resistors are identical, or very close to each other so as to allow the small change caused by the change in thermal conductivity of the surrounding fluid to be distinguished.

In FIG. 4 there are only two temperature sensing elements next to the first heating element. However, it is envisaged that there may be more temperature sensing elements and additional temperature changes in the second heating element.

Figure 5:
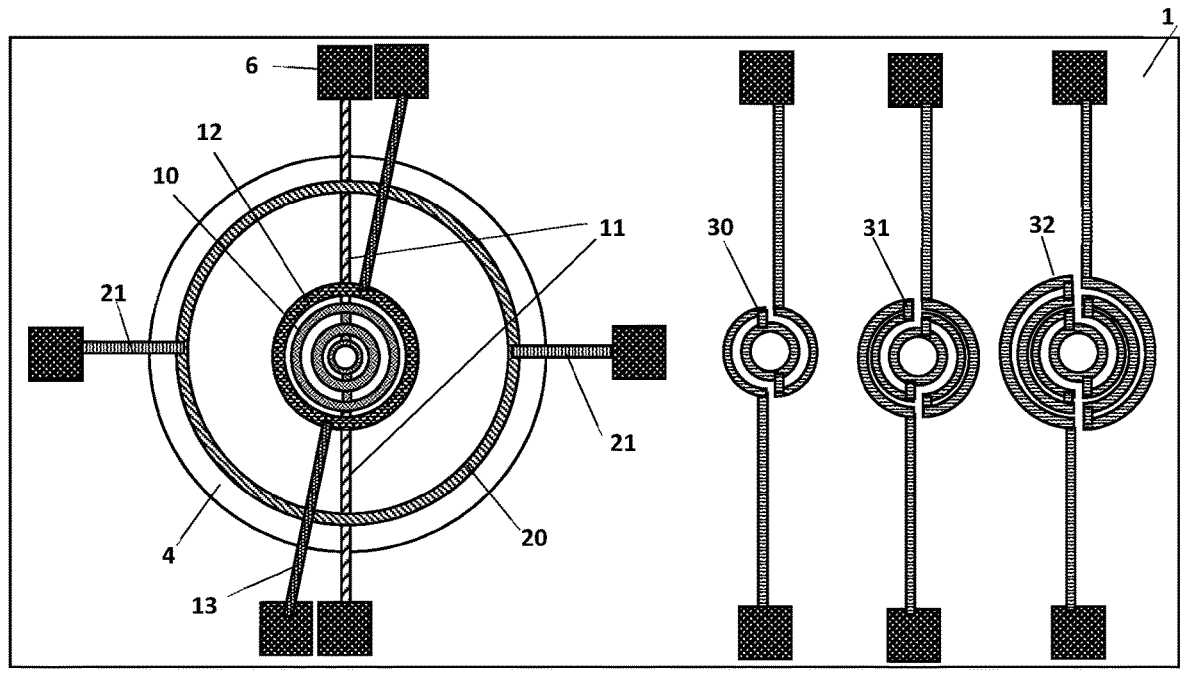
FIG. 5 shows the top view of a thermal conductivity fluid sensor with three additional temperature sensing elements outside the membrane region.

FIG. 5 shows the top view of a thermal conductivity fluid sensor where there is one temperature sensing element 12 next to the second heating element 10, and three resistive temperature sensing elements 30,31,32 outside the membrane region. The resistive temperature sensing elements 30,31,32 each have a different resistance. The resistive temperature sensing elements 30,31,32 perform a similar function to the temperature sensing elements 22A, 22B in FIG. 4, in that they allow differential measurement with the resistive temperature sensing element 12 at different temperature of the second heating element 10.

However since the temperature in this region outside the membrane is not controlled, their resistance will change with changes in ambient temperature and affect the sensor readings. The advantage of this approach is that many more resistors can be accommodated outside the membrane as compared to the limited space on the membrane 4 next to the first heating element 20.

Figure 6:
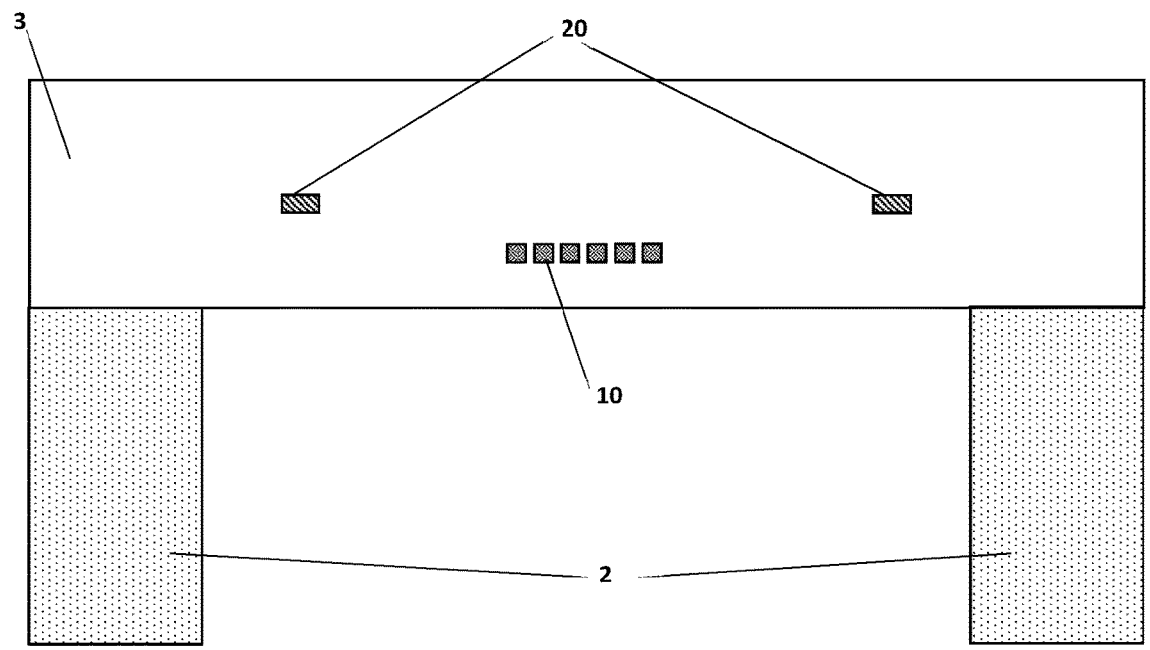
FIG. 6 shows the cross-section of a thermal conductivity fluid sensor comprising two heating elements.

FIG. 6 shows the cross-section of the thermal conductivity fluid sensor shown in FIG. 1. Dielectric layers 3 are supported on a semiconductor substrate 2 with an etched portion. The first and second heating elements 20, 10 are embedded within the dielectric layers.

Figure 7:
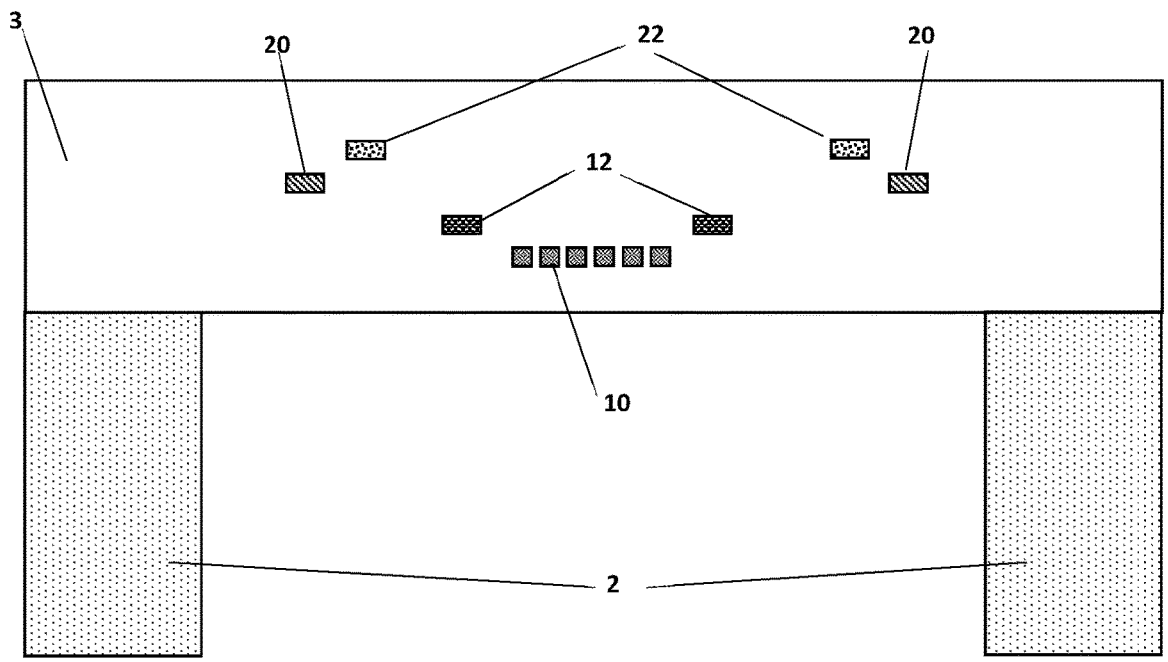
FIG. 7 shows the cross-section of a thermal conductivity fluid sensor comprising two heating elements and two temperature sensing elements.

FIG. 7 shows the cross-section of the thermal conductivity fluid sensor shown in FIG. 2, where in addition to heating elements 20 and 10, there are also two additional temperature sensing elements 12 and 22. All the elements are in different material layers within the dielectric membrane.

The elements shown are all resistive heating elements or resistive temperature sensing elements. These may be made of metals such as aluminium, tungsten, copper, titanium or platinum. Alternatively, they may be polysilicon or single crystal silicon. Alternatively the heating elements can also be transistors, while the temperature sensing elements could be diodes, transistors or thermopiles.

Figure 8:
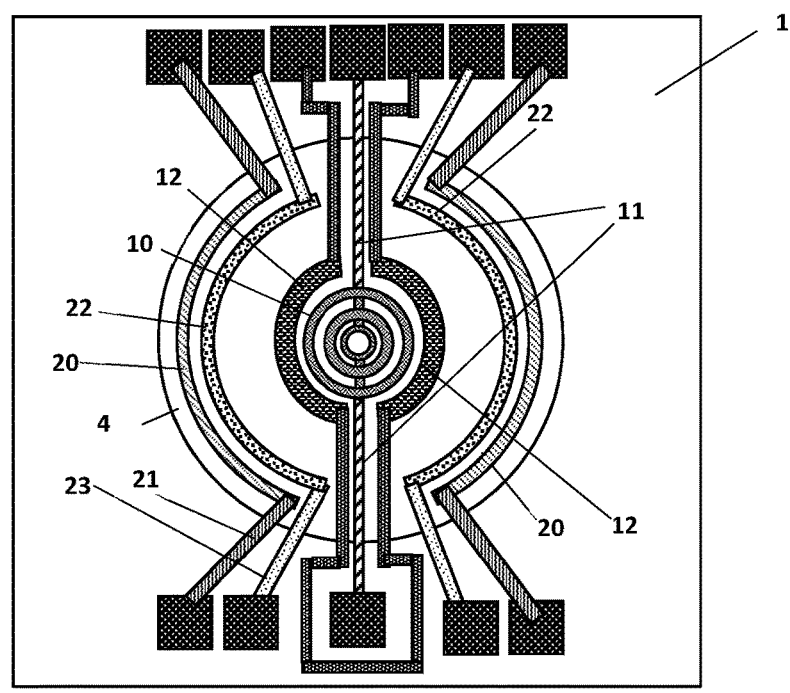
FIG. 8 shows the top-view of another example of the thermal conductivity fluid sensor.

FIG. 8 shows the top view of a thermal conductivity fluid sensor where all the heating and temperature sensing elements are arranged such that they can be made within one layer. For this purpose the temperature sensing element 12 is designed as two halves around second heating element 10, and the tracks for it are designed such that they may go around or surround one of the bond pads of the second heating element. The first heating element and corresponding temperature sensing element are split into two halves. These go into separate bond pads and can be connected together outside the chip.

Figure 9:
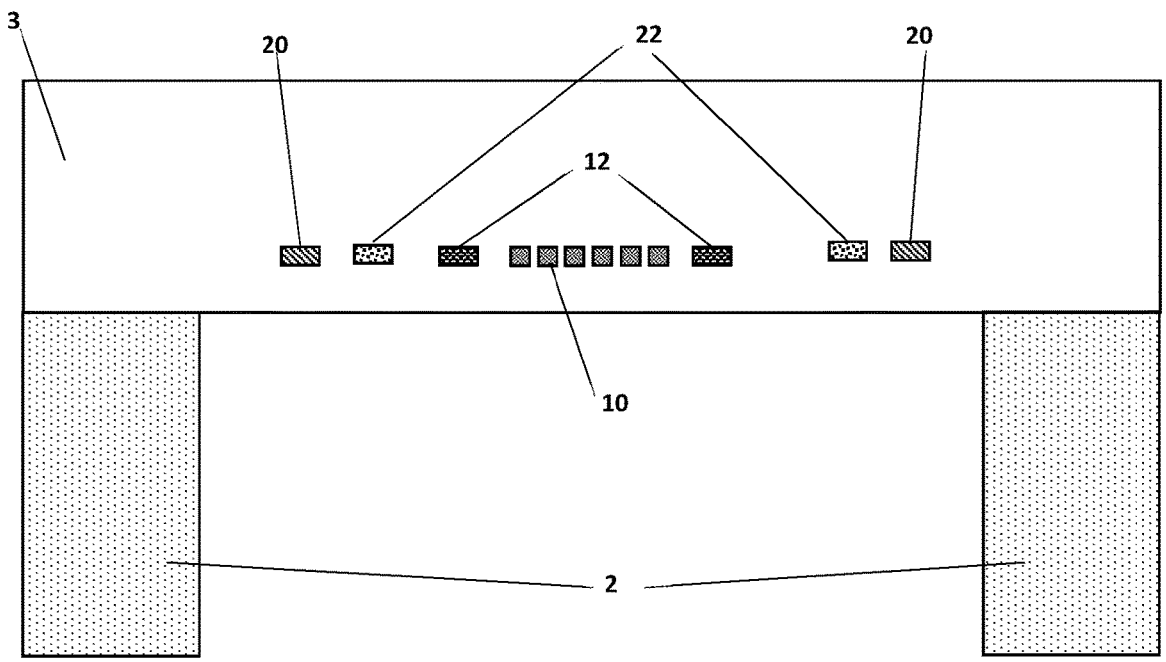
FIG. 9 shows the cross-section of a thermal conductivity fluid sensor where the heating elements and temperature sensing elements are all within the same layer.

FIG. 9 shows the cross-section of the thermal conductivity fluid sensor in FIG. 8, and all the elements are within one material layer.

Figure 10:
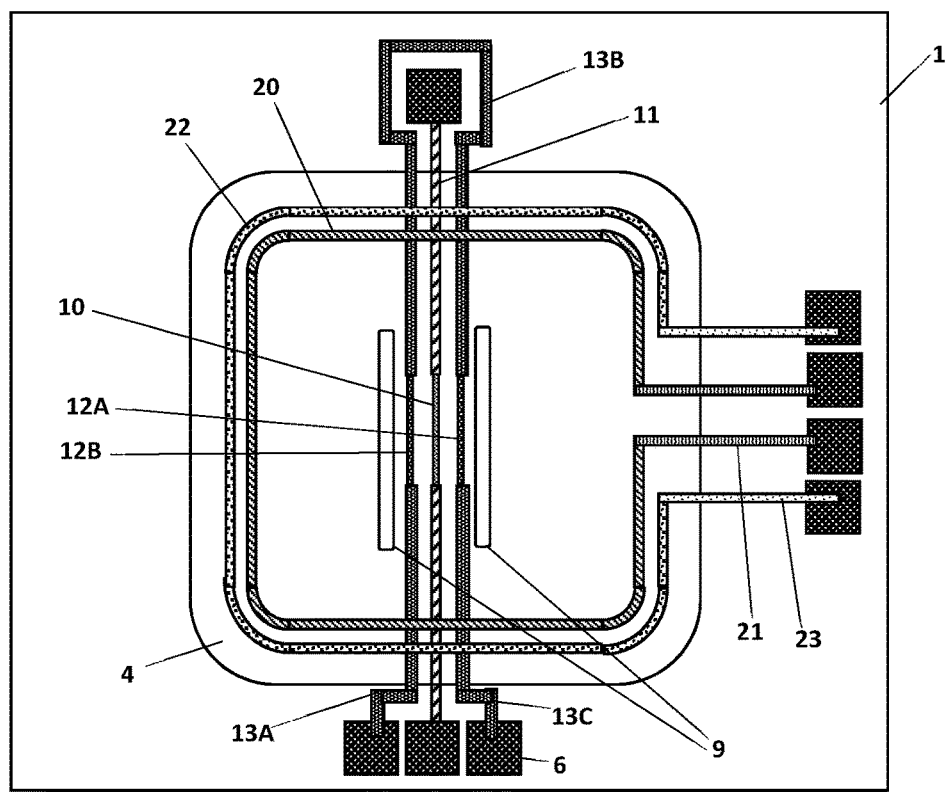
FIG. 10 shows the top-view of an example of a thermal conductivity fluid sensor with a rectangular membrane and a wire shaped second heating element.

FIG. 10 shows yet another top view of a thermal conductivity fluid sensor. In this case, the membrane 4 has a shape of a square with rounded corners. The first heating element 20 is a ring close to the periphery of the membrane and has a shape similar to the membrane. The temperature sensing element 22 is next to heating element 20 and has a similar shape to the heating element 20. The second heating element 10 is a hot-wire heater, and connected to bond pads 6 by tracks 11. A temperature sensing element next to the second heating element is split into two parts—12A and 12B on either side of the second heating element. Tracks for temperature sensing element 13A, 13B, 13C connect them together and to the bond pads. Track 13B in particular connects 12A and 12B and goes around one of the bond pads of the second heating element. In this configuration the first heating element 20 and temperature sensing element 22 can be on one layer, while the second heating element 10 and temperature sensing elements 12A, 12B can be in another layer.

Figure 11:
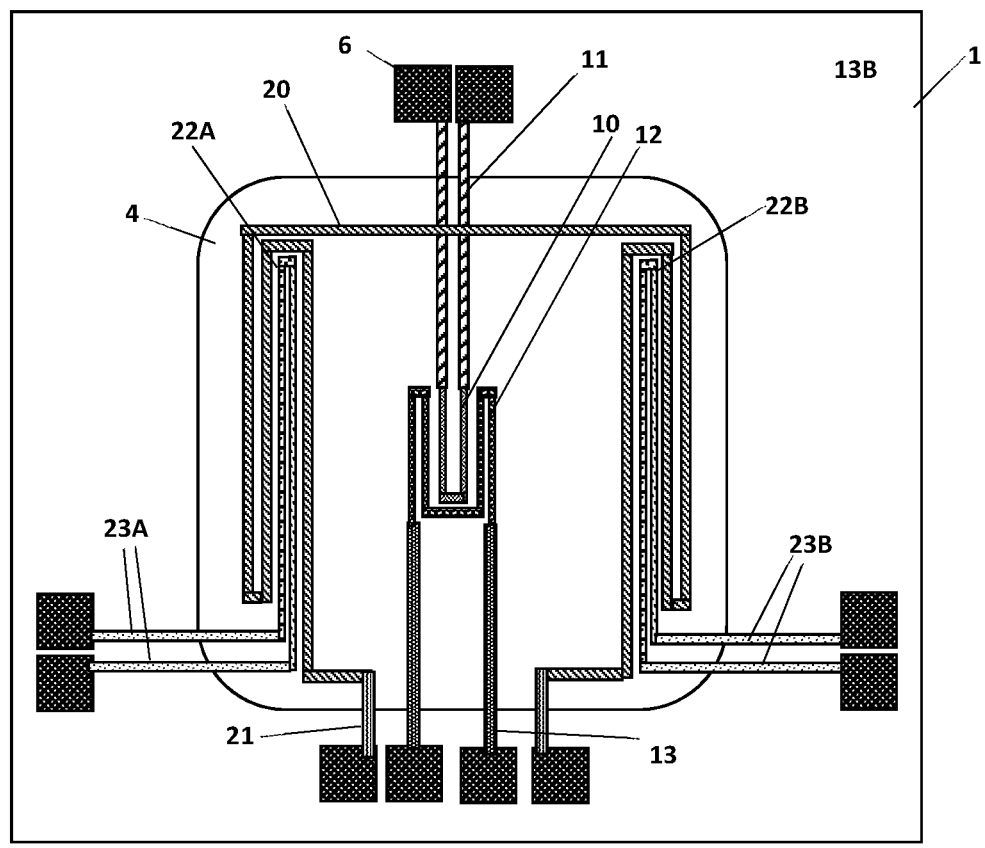
FIG. 11 shows the top-view of a thermal conductivity fluid sensor showing another possible shape of heating and temperature sensing elements.

FIG. 11 shows the top view of another design of the thermal conductivity fluid sensor. The first heating element 20 is arranged around the periphery of the membrane, but has a meander shape on two sides with space for temperature sensing elements 23A and 23B. The second heating element 10 is meander shape in the centre of the membrane with one bend—however it is envisaged that more bends are also possible. The temperature sensing element 12 also has a meander shape in the centre of the membrane but with a gap for the second heating element. The design of the second heating elements 10 and the temperature sensing element 12 is such that their tracks 11, 13 are on opposite sides.

Figure 12:
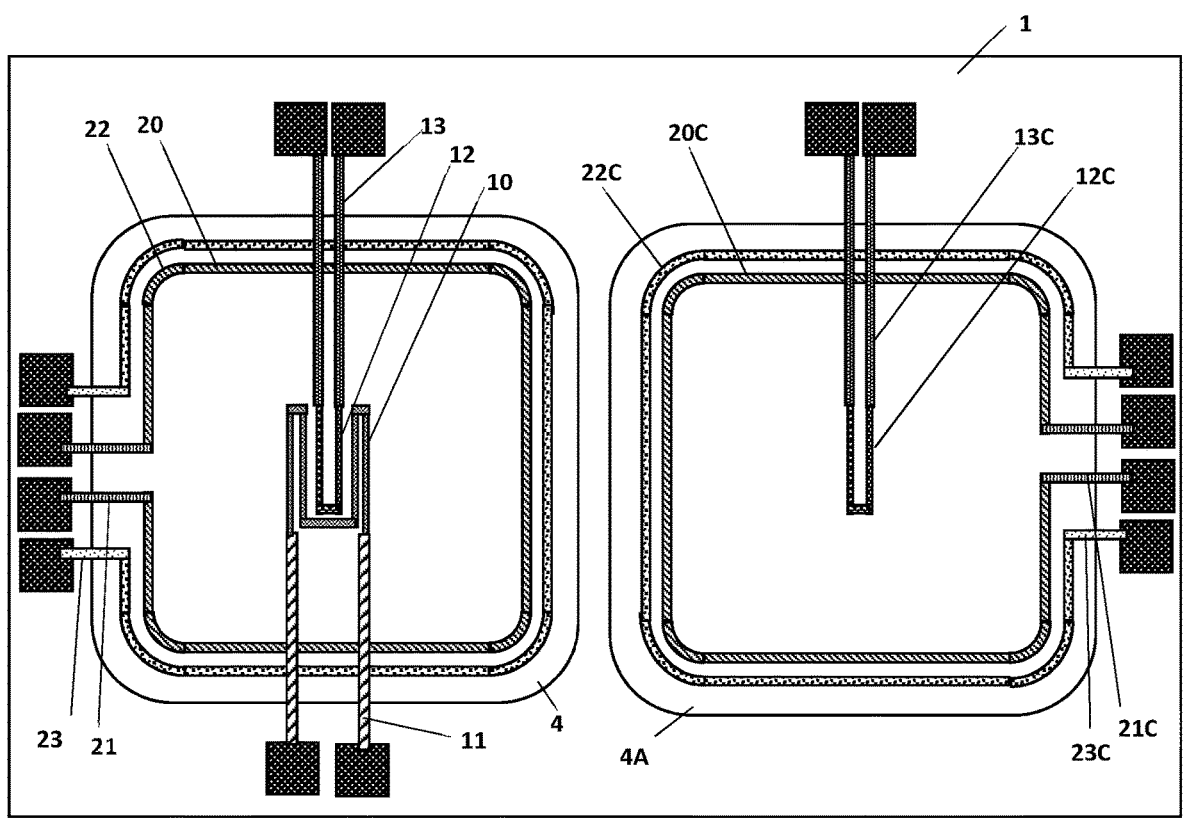
FIG. 12 shows the top-view of a thermal conductivity fluid sensor comprising two membranes with one of them without a heater to act as a reference.

FIG. 12 shows the top view of a thermal conductivity fluid sensor comprising an additional reference membrane. In this design there are two membranes 4, 4A. Membrane 4 is the main sensor membrane comprising a first heating element 20, a first temperature sensing element 22, a second heating element 10 and a second temperature sensing element 12. The second heating element 10 is a meander shape with a gap to allow the second temperature sensing element 12 within it. Membrane 4A is a reference membrane and comprises a heating element 20C, a first temperature sensing element 22C, and a second temperature sensing element 12C. However, it does not have a second heating element. This allows a differential measurement to be made between the temperature sensing elements 12 and 12C.

Figure 13:
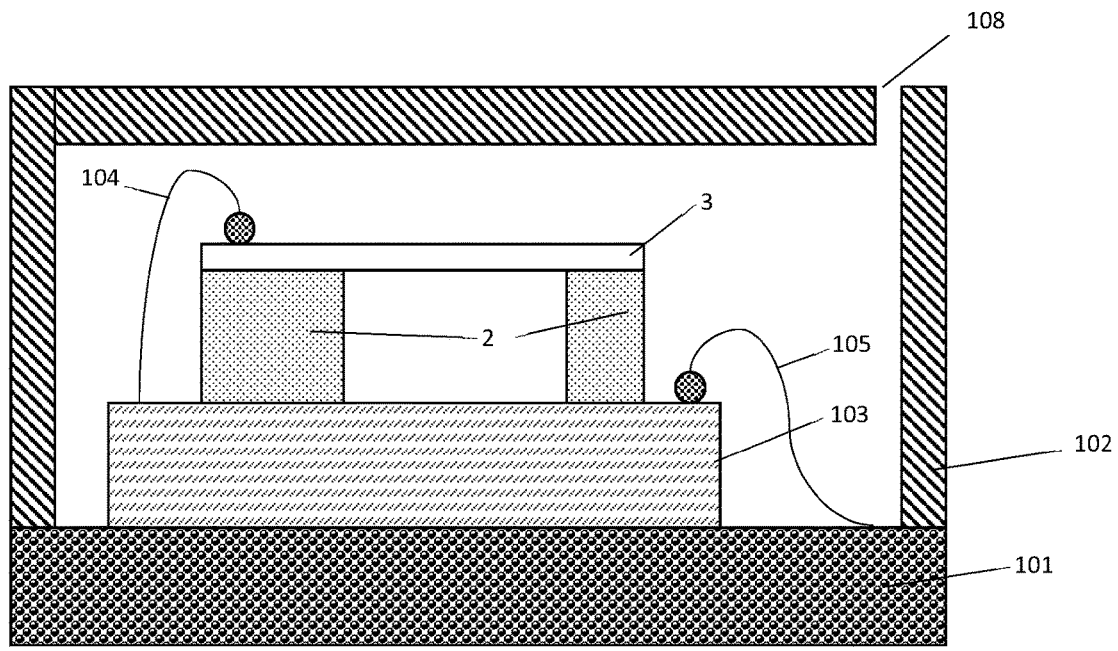
FIG. 13 shows the cross-section of a thermal conductivity fluid sensor package comprising a sensor chip above an ASIC chip and both within a package.

FIG. 13 shows a cross-section of a thermal conductivity fluid sensor assembly. It comprises a package base 101 and a package lid 102. Within the package is an ASIC (Application Specific Integrated Circuit) chip 103 that is used to control and measure the thermal conductivity sensor chip. Above this ASIC chip 103 is the thermal conductivity sensor chip comprising a substrate 2 and dielectric region or layer 3. The sensor chip may include any fluid sensor as described above. Wire bonds 104 electrically connect the thermal conductivity sensor fluid chip to the ASIC chip 103, and wire bonds 105 electrically connect the ASIC 103 to the package base 101. A hole 108 within the package lid 102 allows the ambient air or gas to diffuse into the package and around the thermal conductivity sensor. More than one hole may be present within the package lid, and the size and shape of the hole 108 can be varied, and filters may be placed around or within the hole 108 or holes to protect against particles or liquids.

Figure 14:
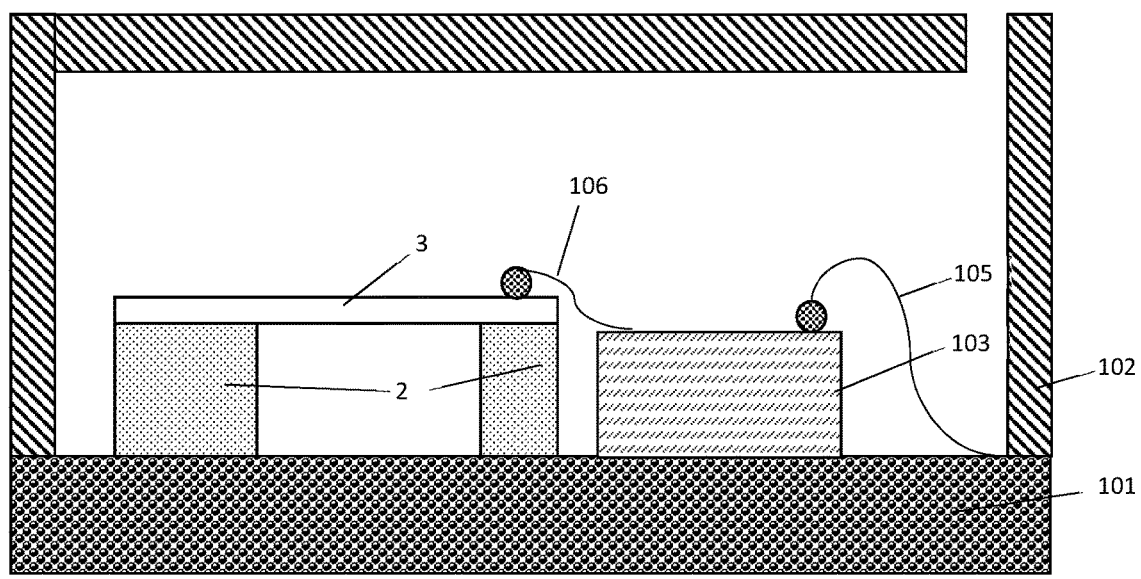
FIG. 14 shows the cross-section of a thermal conductivity fluid sensor package with the sensor chip and ASIC side by side.

FIG. 14 shows a cross-section of an alternative thermal conductivity fluid sensor assembly. The ASIC chip 103 and the fluid sensor chip are not stacked on top of each other, but are located side by side within the package. Wire bonds 106 connect the sensor chip to the ASIC chip 103.

Figure 15:
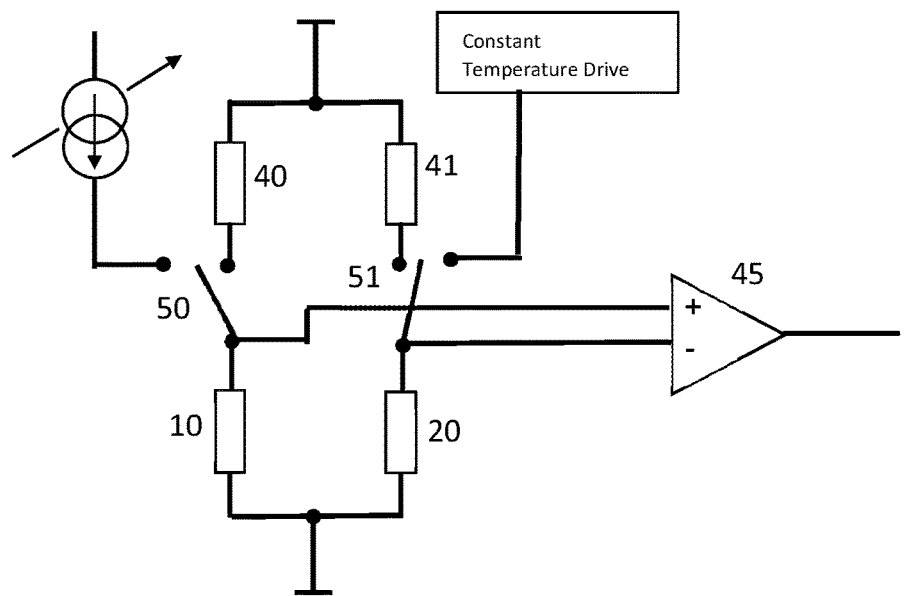
FIG. 15 shows an example circuit of a thermal conductivity fluid sensor where the heating element also acts as temperature sensing elements.

FIG. 15 shows a circuit diagram of a thermal conductivity fluid sensor for the design in FIG. 1 where the heating elements also act as the temperature sensing elements. The circuit has a Wheatstone bridge comprising the first heating element 20 and the second heating element 10 and two fixed resistors 40, 41. A differential amplifier 45 is at the output of the Wheatstone bridge. Switch 51 can be used to disconnect the first heating element 20 from the wheatstone bridge and connect to a constant temperature circuit. Similarly a switch 50 can be used to disconnect the second heating element 10 from the Wheatstone bridge circuit and connect to a constant current source. The switches 50,51 can be electronic switches made from transistors. The differential amplifier 45 can be an instrumentation amplifier.

Figure 16:
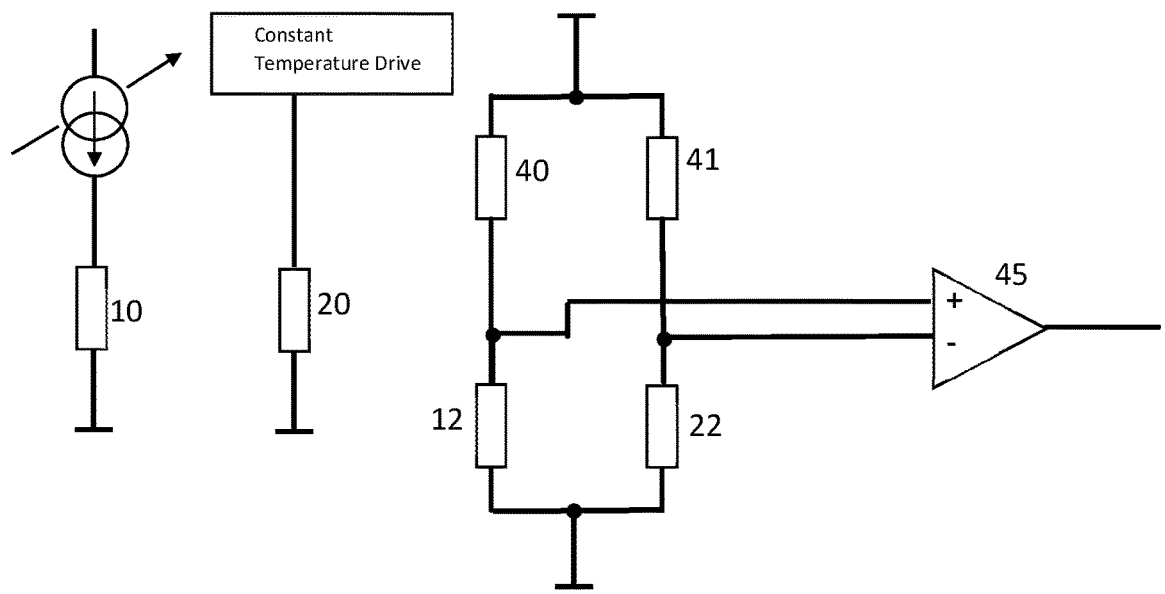
FIG. 16 shows an example circuit of a thermal conductivity fluid sensor where the heating elements and temperature sensing elements are separate.

FIG. 16 shows a circuit diagram of a thermal conductivity fluid sensor where the temperature sensing elements are separate from the heating elements. In this case the first heating element 20 and second heating element 10 are directly connected to constant temperature and constant current drive circuits without the need for any switches. And the wheatstone bridge now comprises the first temperature sensing element 22, the second temperature sensing element 12 and two fixed resistors 40,41.

Figure 17:
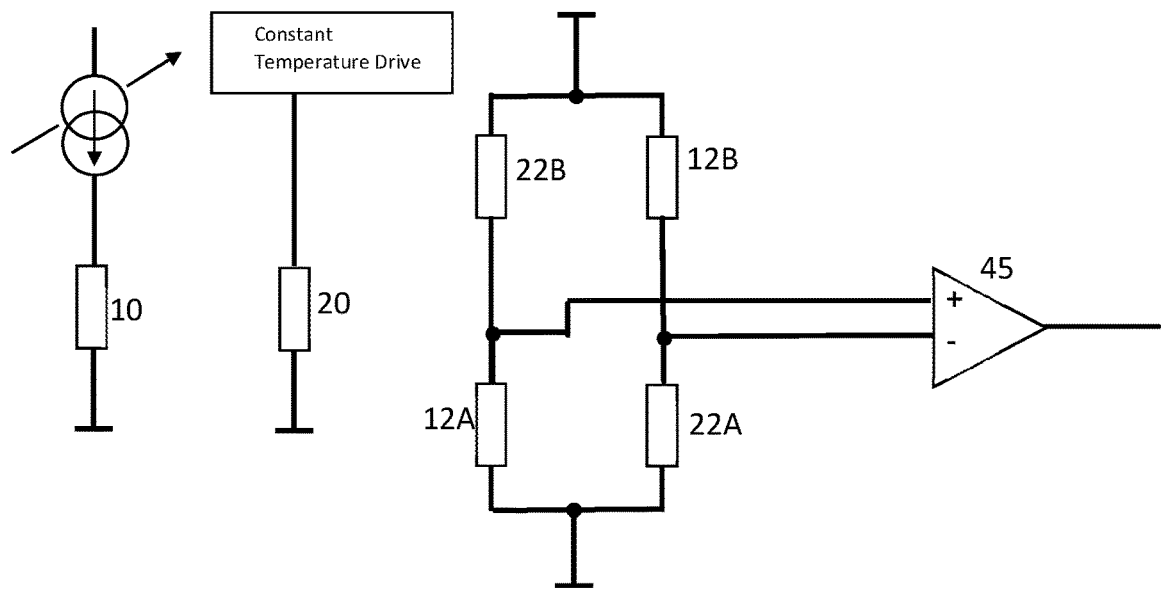
FIG. 17 shows an example circuit of a thermal conductivity fluid sensor where each heating element has two temperature sensing elements next to it.

FIG. 17 shows a circuit diagram of a thermal conductivity fluid sensor where there are two temperature sensing elements next to each heating element, such as the design shown in FIG. 3. In this case there is no need for fixed resistors within the Wheatstone bridge, and it comprises the four temperature sensing elements 12A, 12B, 22A, 22B. Such a method doubles the sensitivity of the circuit.

Figure 18:
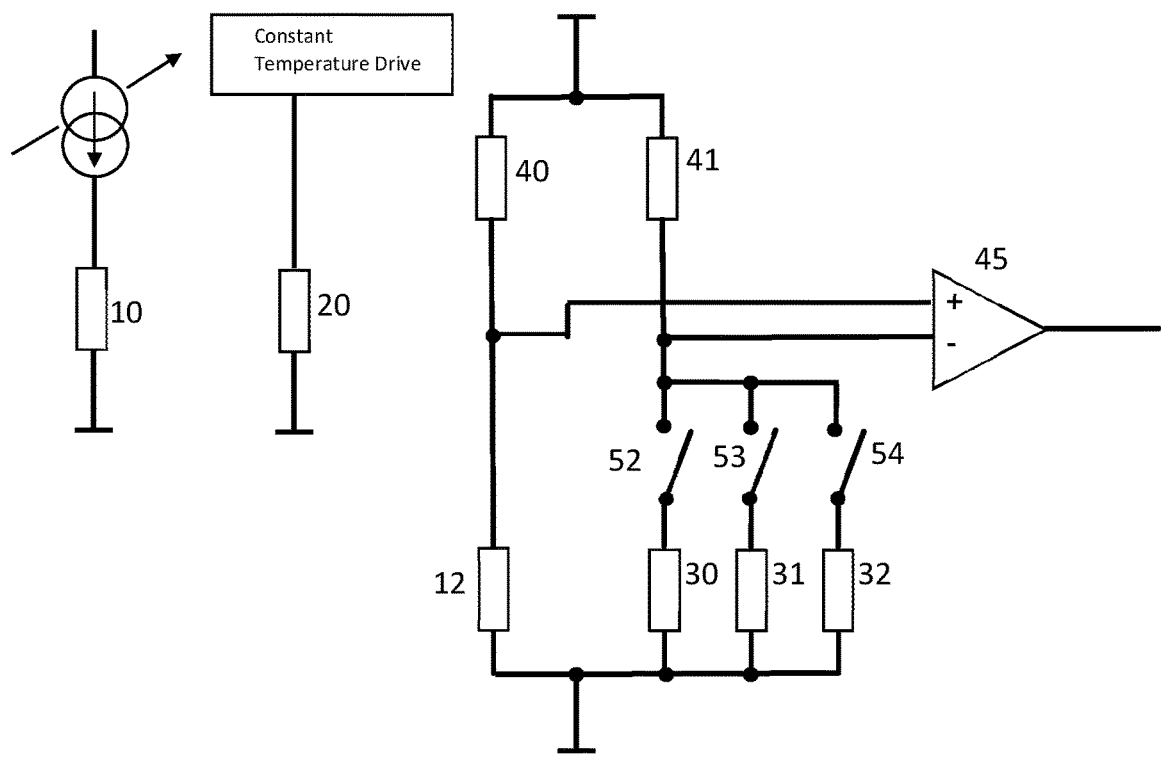
FIG. 18 shows an example circuitry of a thermal conductivity fluid sensor where there are three resistive temperature sensing elements with different resistances either next to the first heating element, or outside the membrane region.

FIG. 18 shows a circuit diagram of a thermal conductivity fluid sensor where the temperature sensing element 12 can be differentially compared to more than one resistor. This is shown as an example for the design shown in FIG. 5, but can also apply to the design shown in FIG. 4. The Wheatstone bridge allows selection of one of the resistors 30,31,32 by use of electronic switches 52,53,54. The resistors can be selected based on the bias on the second heating element, with the resistor values chosen such that at the applied bias values the resistance of the temperature sensing element 12 is similar to one of the resistors 30,31,32.

Figure 19:
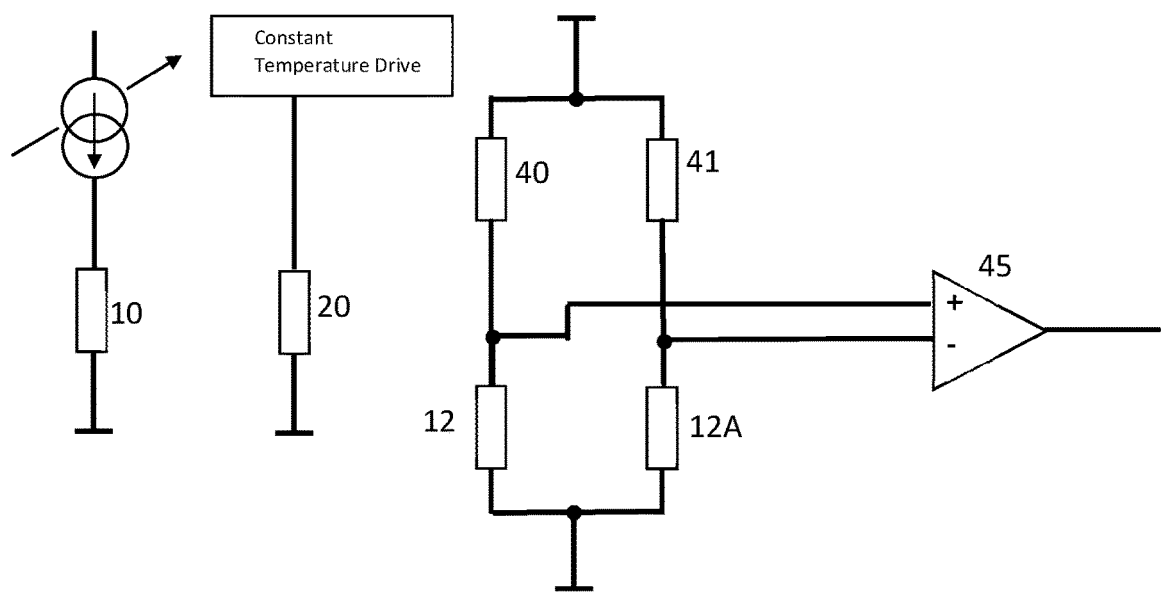
FIG. 19 shows an example circuitry of a thermal conductivity fluid sensor with a reference membrane.

FIG. 19 shows a circuit diagram of a thermal conductivity fluid sensor where there is a reference membrane such as the design in FIG. 12. In this case, the differential measurement is done between the second temperature sensing element 12 on the main membrane, and second temperature sensing element 12C on the reference membrane.

It should be noted that for all these circuit designs the second heating element 10 is shown as connected to a constant current source as an example. It can also be connected to a constant voltage or constant power source.

The skilled person will understand that in the preceding description and appended claims, positional terms such as 'above', 'overlap', 'under', 'lateral', etc. are made with reference to conceptual illustrations of a device, such as those showing standard cross-sectional perspectives and those shown in the appended drawings. These terms are used for ease of reference but are not intended to be of limiting nature. These terms are therefore to be understood as referring to a device when in an orientation as shown in the accompanying drawings.

Although the disclosure has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the disclosure, whether alone or in any appropriate combination with any other feature disclosed or illustrated herein.

Reference Numerals

| | |
|---|---|
| 1 Semiconductor chip | 22 First Temperature sensing Element |
| 2 Semiconductor Substrate | 22A, 22B Parts of First Temperature sensing |

| Reference Numerals | |
|---|---|
| 3 Dielectric Layer | Element |
| 4 Dielectric membrane | 22C Additional First Temperature sensing element |
| 4A Additional dielectric membrane | |
| 6 Bond pads | 23 Tracks to First temperature sensing element |
| 9 Recessed Regions | 30, 31, 32 Resistors outside the membrane |
| 10 Second Heating Element | 40, 41 Additional resistor |
| 11 Tracks to Second Heating Element | 45, Differential Amplifier |
| 12 Second Temperature sensing Element | 50, 51, 52, 53, 54 Switches |
| 12A, 12B Parts of Second Temperature sensing Element | 101 Package base |
| | 102 Package lid |
| 12C Additional Second Temperature sensing element | 103 ASIC |
| | 104, 105 Wire bonds |
| 13 Tracks to second temperature sensing element | 106 Inlet |
| | 107 Outlet |
| 20 First Heating Element | 108 Hole through package lid110 Lid |
| 20C Additional First heating Element | |
| 21 Tracks to First Heating Element | |
| 21C Tracks to additional First Heating Element | |

The invention claimed is:

1. A fluid sensor for sensing a concentration or composition of a fluid, the sensor comprising:
a semiconductor substrate comprising a first etched portion;
a dielectric region located on the semiconductor substrate, wherein the dielectric region comprises a first dielectric membrane located over the first etched portion of the semiconductor substrate;
a first heating element located within the first dielectric membrane; and
a second heating element;
wherein the first heating element is arranged to thermally shield the second heating element from ambient temperature changes;
wherein the first heating element or the second heating element is configured to operate as a temperature sensing element;
wherein the first heating element is configured to operate in a constant temperature or constant resistance mode;
wherein the second heating element is configured to operate in a constant current or constant voltage mode or constant power mode; and
wherein the sensor is configured to determine a thermal conductivity of the fluid using the temperature sensing element to determine said concentration or composition of the fluid.

2. A fluid sensor for sensing a concentration or composition of a fluid, the sensor comprising:
a semiconductor substrate comprising at least one etched portion;
a dielectric region located on the semiconductor substrate, wherein the dielectric region comprises a first dielectric membrane located over the first etched portion of the semiconductor substrate;
a first heating element located within the first dielectric membrane;
a second heating element;
a first temperature sensing element positioned with the first heating element; and
a second temperature sensing element positioned with the second heating element;
wherein the first heating element is arranged to thermally shield the first and second temperature sensing elements and the second heating element from ambient temperature changes;
wherein the first heating element is configured to operate in a constant temperature or constant resistance mode; and
wherein the second heating element is configured to operate in a constant current or constant voltage mode or constant power wherein a separation between the second temperature sensing element and the first temperature sensing element introduces a temperature difference between the second temperature sensing element and the first temperature sensing element, such that a differential signal between the first temperature sensing element and the second temperature sensing element is indicative of the concentration or composition of the fluid based on a thermal conductivity of the fluid.

3. A fluid sensor according to claim 1, wherein the second heating element is located within the first dielectric membrane, or wherein the second heating element is located within a second dielectric membrane.

4. A fluid sensor according claim 1, wherein the second heating element is configured to operate at higher temperature than the first heating element.

5. A fluid sensor according to claim 1, wherein the first dielectric membrane comprises at least one recessed region configured to thermally isolate the first heating element from the second heating element.

6. A fluid sensor according to claim 5 wherein the at least one recessed region comprises holes or perforations in the first dielectric membrane.

7. A fluid sensor according to claim 1 wherein the first and second heating elements are arranged in one of the following configurations:
(i) the second heating sensing element is located closer to a centre of the first dielectric membrane and the first heating element is located closer to an edge of the first dielectric membrane; or
(ii) wherein the first and the second heating elements are located within the first dielectric membrane and the first heating element surrounds the second heating element.

8. A fluid sensor according to claim 2, wherein the first temperature sensing element and the second temperature sensing elements are located on or within the first dielectric membrane, and wherein at least one recessed region is laterally located between the first temperature sensing element and the second temperature sensing element.

9. A fluid sensor according to claim 1, wherein the first temperature sensing element and the first heating element are located within the first dielectric membrane, and wherein a second temperature sensing element and the second heating element are located within a second dielectric membrane.

10. A fluid sensor according to claim 9 comprising a third heating element configured to operate in a constant temperature or in a constant resistance mode located within the same dielectric membrane as the second heating element.

11. A fluid sensor according to claim 2, wherein a maintained temperature of the first temperature sensing element during use is the same as a maintained temperature of the first heating element and wherein a maintained temperature of the second temperature sensing element during use is the same as a maintained temperature of the second heating element.

12. A fluid sensor according to claim 2, comprising further temperature sensing elements positioned with the first heating element, wherein a maintained temperature of the first and further temperature sensing elements during use is the same as a maintained temperature of the first heating element.

13. A fluid sensor according to claim 2, comprising further temperature sensing element positioned with the second heating element, wherein a maintained temperature of the second and further temperature sensing elements is the same as a maintained temperature of the second heating element.

14. A fluid sensor according claim 1,
wherein one of the first temperature sensing element or a second temperature sensing element or the first or second heating elements are located in a same layer of the dielectric region and wherein the first temperature sensing element or the second temperature sensing element laterally surrounds the first and second heating elements respectively, or
wherein the first temperature sensing element or the second temperature sensing element is located below or above the first or second heating elements respectively.

15. A fluid sensor according to claim 1, wherein at least one of the first and second heating element is a resistive heating element; and/or wherein at least one of the first temperature sensing element and a second temperature sensing element are resistive temperature detector elements.

16. A fluid sensor according to claim 1, further comprising circuitry configured to determine the concentration or composition of the fluid based on a differential signal between any of:
the first heating element
the second heating element
the first temperature sensing element
a second temperature sensing element; and
optionally wherein the first heating element, the second heating element, the first temperature sensing element, the second temperature sensing element, and the circuitry are positioned on a chip.

17. A fluid sensor according to claim 16, wherein the circuitry comprises one or more of:
a constant current or constant resistor drive circuit,
a constant current source,
a Wheatstone bridge,
an amplifier, an Analogue to Digital convertor,
a Digital to Analogue Convertor, or
a microcontroller.

18. A fluid sensor according to claim 16, wherein the first temperature sensing element and the second temperature sensing element are located on two sides of a bridge circuit, and wherein the sensor is configured such that an output of the bridge circuit is a function of the thermal conductivity of the fluid around the sensor.

19. A fluid sensor according to claim 1, wherein the first etched portion of the semiconductor substrate has sloped sidewalls; and/or wherein the first etched portion of the semiconductor substrate extends only partially through the depth of the semiconductor substrate.

20. A fluid sensor according to claim 1, wherein the semiconductor substrate comprises additional etched portions, and wherein the dielectric layer comprises additional dielectric membranes located over the additional etched portion of the semiconductor substrate, and
wherein the sensor further comprises:
additional heating elements located within the additional dielectric membrane; and
additional temperature sensing element located in additional corresponding dielectric membranes.

21. A fluid sensor according to claim 20, wherein the first heating element and the additional heating element are connected in series, and/or wherein the first temperature sensing element and the additional temperature sensing element are connected in series.

22. A fluid sensor according to claim 20, wherein the first or second heating element and at least one of the additional heating elements are configured to operate at different temperatures.

23. A fluid sensor according to claim 1, further comprising a covering located on a surface of the sensor, wherein the covering comprises a hole configured to allow fluid to travel from an outer surface of the covering to the fluid channel above the first dielectric membrane.

24. A fluid sensor according to claim 1, further comprising at least one further temperature sensing element located outside the membrane region, above the semiconductor substrate.

25. A fluid sensor according to claim 1, further comprising a pair of further temperature sensing elements located on the first dielectric membrane, wherein a first temperature sensing element of the pair of temperature sensing elements is located on a first side of the second heating element and a second temperature sensing element of the pair of temperature sensing elements is located on a second side of the second heating element.

26. A sensor assembly comprising the fluid sensor of claim 1 and an application specific integrated circuit (ASIC) coupled to the sensor.

27. A sensor assembly according to claim 26, comprising:
a fluid sensor housing;
wherein the fluid sensor is located within the fluid sensor housing.

28. A sensor assembly according to claim 27, wherein the fluid sensor is packaged on a printed circuit board or another semiconductor substrate in a flip-chip configuration.

29. A method of measuring a concentration or composition of a fluid using a sensor of claim 2, the method comprising:
applying a constant electrical bias or constant current or constant power to the second heating element; and
monitoring the temperature or the resistance of the first or second temperature sensing element.

30. A method according to claim 29, the method comprising:
applying an electrical bias to the first heating element through a feedback loop control circuit to maintain a constant resistance or a constant temperature of the first heating element; wherein a differential signal between the first temperature sensing element with respect to the second temperature sensing element is indicative of the concentration or composition of the fluid based on a thermal conductivity of the fluid.

* * * * *